(12) United States Patent
Carlsson et al.

(10) Patent No.: US 11,471,659 B2
(45) Date of Patent: Oct. 18, 2022

(54) CONNECTOR SYSTEM WITH A FEMALE CONNECTOR AND A MALE CONNECTOR, AND A SYSTEM INCLUDING A PLURALITY OF THE CONNECTOR SYSTEMS

(71) Applicant: GAMBRO LUNDIA AB, Lund (SE)

(72) Inventors: Ola Carlsson, Lund (SE); Hans Peder Flank, Bjärred (SE)

(73) Assignee: Gambro Lundia AB, Lund (SE)

( * ) Notice: Subject to any disclaimer, the term of this patent is extended or adjusted under 35 U.S.C. 154(b) by 532 days.

(21) Appl. No.: 16/345,130

(22) PCT Filed: Oct. 25, 2017

(86) PCT No.: PCT/EP2017/077231
§ 371 (c)(1),
(2) Date: Apr. 25, 2019

(87) PCT Pub. No.: WO2018/077917
PCT Pub. Date: May 3, 2018

(65) Prior Publication Data
US 2019/0282794 A1    Sep. 19, 2019

(30) Foreign Application Priority Data
Oct. 25, 2016 (SE) ...................... 1651392-1

(51) Int. Cl.
*A61M 39/10*     (2006.01)
*F16L 15/00*     (2006.01)

(52) U.S. Cl.
CPC ........ *A61M 39/1011* (2013.01); *F16L 15/006* (2013.01); *A61M 2039/1033* (2013.01);
(Continued)

(58) Field of Classification Search
CPC ...... A61M 2039/1033; A61M 39/1011; A61M 2039/1083; A61M 2039/1088; A61M 2039/1094
See application file for complete search history.

(56) References Cited

U.S. PATENT DOCUMENTS

| 3,287,031 A | 11/1966 | Simmons et al. |
| 4,824,145 A * | 4/1989 | Carlsson ................. F16L 37/12 285/38 |

(Continued)

FOREIGN PATENT DOCUMENTS

| EP | 3714934 A1 * | 9/2020 | ............ A61M 39/20 |
| WO | 1999064103 | 12/1999 | |

(Continued)

OTHER PUBLICATIONS

International Search Report for International Application No. PCT/EP2017/077231 dated Jan. 17, 2018; (3 pages).

*Primary Examiner* — David Bochna
(74) *Attorney, Agent, or Firm* — K&L Gates LLP

(57) ABSTRACT

A connector system (47, 48, 49, 50) for a medical application including a male single channel fluid connector (X) designed with an outer collar (M2) arranged concentric with an inner tube (3) and extending beyond a center collar (M1), and a female single channel fluid connector (Y) is designed with an outer collar (F1) arranged concentric with a tube (13), wherein the male single channel fluid connector (X) is interconnectable with the female single channel fluid connector (Y) to thereby form a fluid tight single channel connection for passage of fluid, and to a luer type female single channel fluid connector (YS), and wherein the female single channel fluid connector (Y) is interconnectable with a luer type male single channel fluid connector (XS). Also a system including a plurality of the connector systems is disclosed.

13 Claims, 13 Drawing Sheets

(52) U.S. Cl.
CPC ............... *A61M 2039/1083* (2013.01); *A61M 2039/1088* (2013.01); *A61M 2039/1094* (2013.01); *A61M 2210/1017* (2013.01)

(56) References Cited

U.S. PATENT DOCUMENTS

| | | | |
|---|---|---|---|
| 5,176,415 A * | 1/1993 | Choksi | A61M 39/10 |
| | | | 128/202.27 |
| 5,725,511 A | 3/1998 | Urrutia | |
| 5,947,937 A | 9/1999 | Urrutia et al. | |
| 2003/0153865 A1* | 8/2003 | Connell | A61M 39/14 |
| | | | 604/28 |
| 2008/0132876 A1 | 6/2008 | Felt | |
| 2008/0172039 A1* | 7/2008 | Raines | A61M 39/1011 |
| | | | 604/533 |
| 2008/0214990 A1* | 9/2008 | Smutney | A61M 3/0208 |
| | | | 604/27 |
| 2008/0287919 A1 | 11/2008 | Kimball | |
| 2009/0099552 A1 | 4/2009 | Levy et al. | |
| 2011/0208160 A1 | 8/2011 | Wu et al. | |
| 2013/0158521 A1 | 6/2013 | Sobue | |
| 2013/0245611 A1 | 9/2013 | Bonnet et al. | |
| 2014/0276651 A1 | 9/2014 | Schultz | |

FOREIGN PATENT DOCUMENTS

| | | | |
|---|---|---|---|
| WO | 2012098736 | 7/2012 | |
| WO | 2012170961 | 12/2012 | |
| WO | 2013068393 | 5/2013 | |
| WO | WO-2016174032 A1 * | 11/2016 | ............ A61M 39/10 |

* cited by examiner

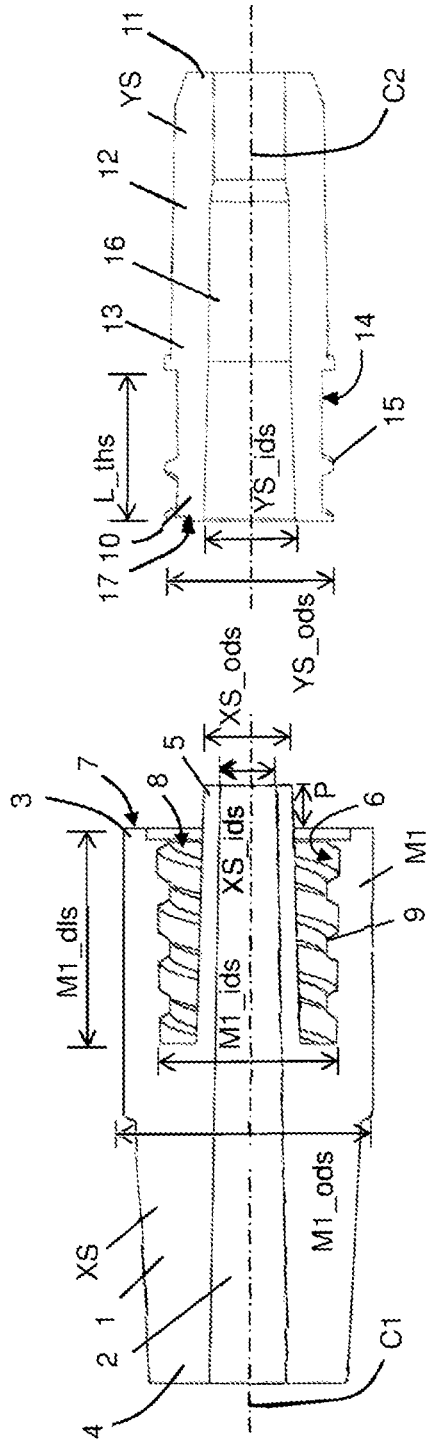
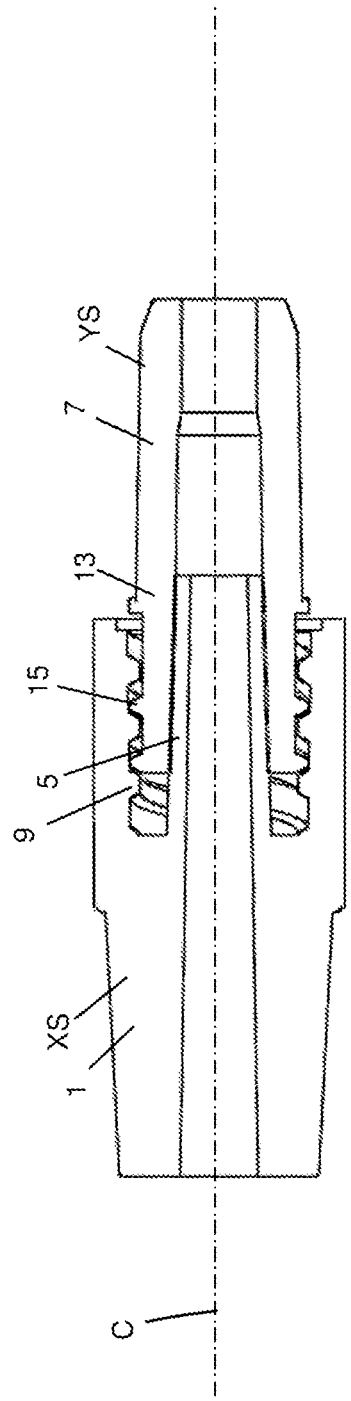
FIG. 1 (PRIOR ART)
FIG. 2 (PRIOR ART)
FIG. 3 (PRIOR ART)

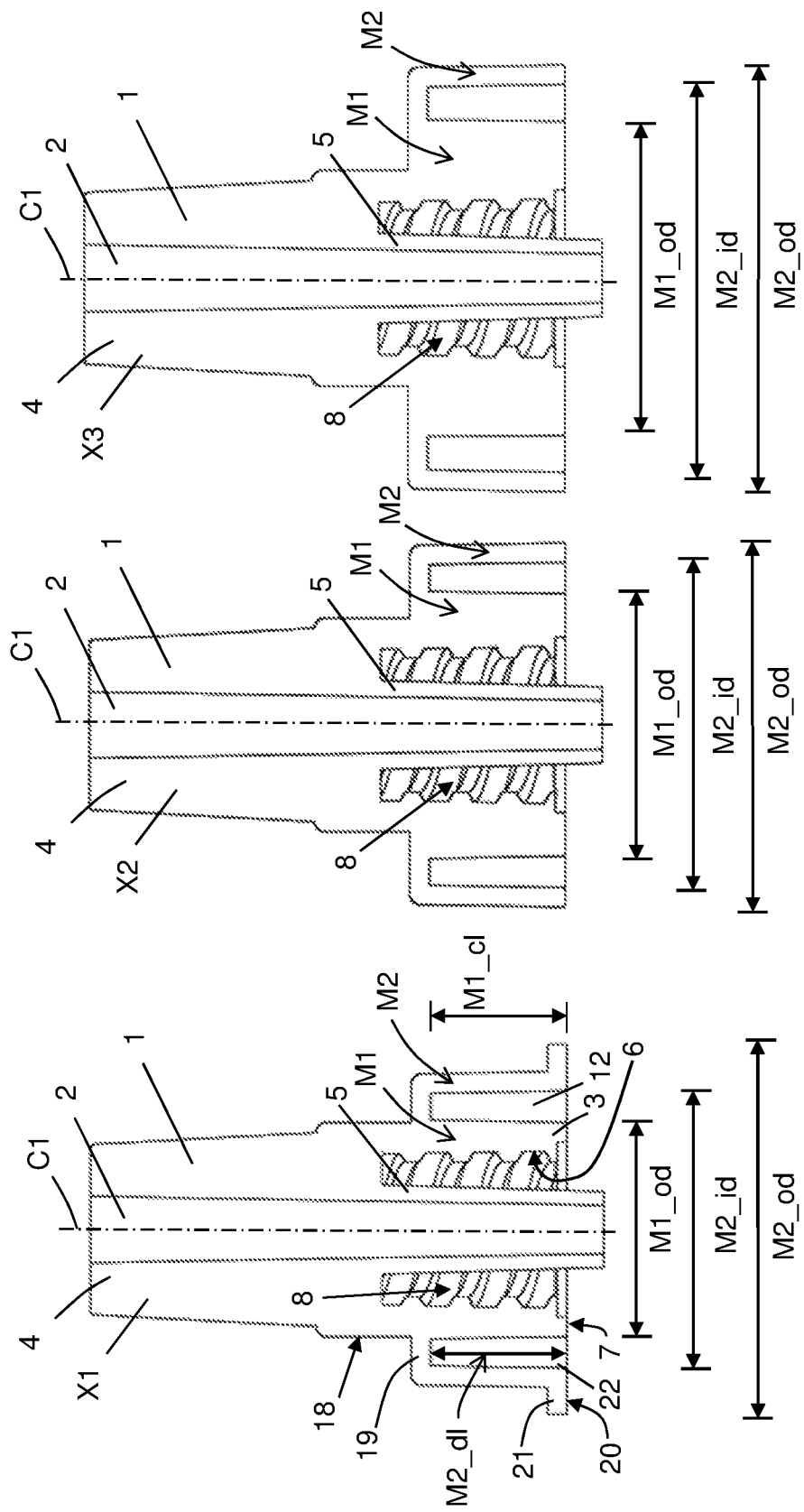

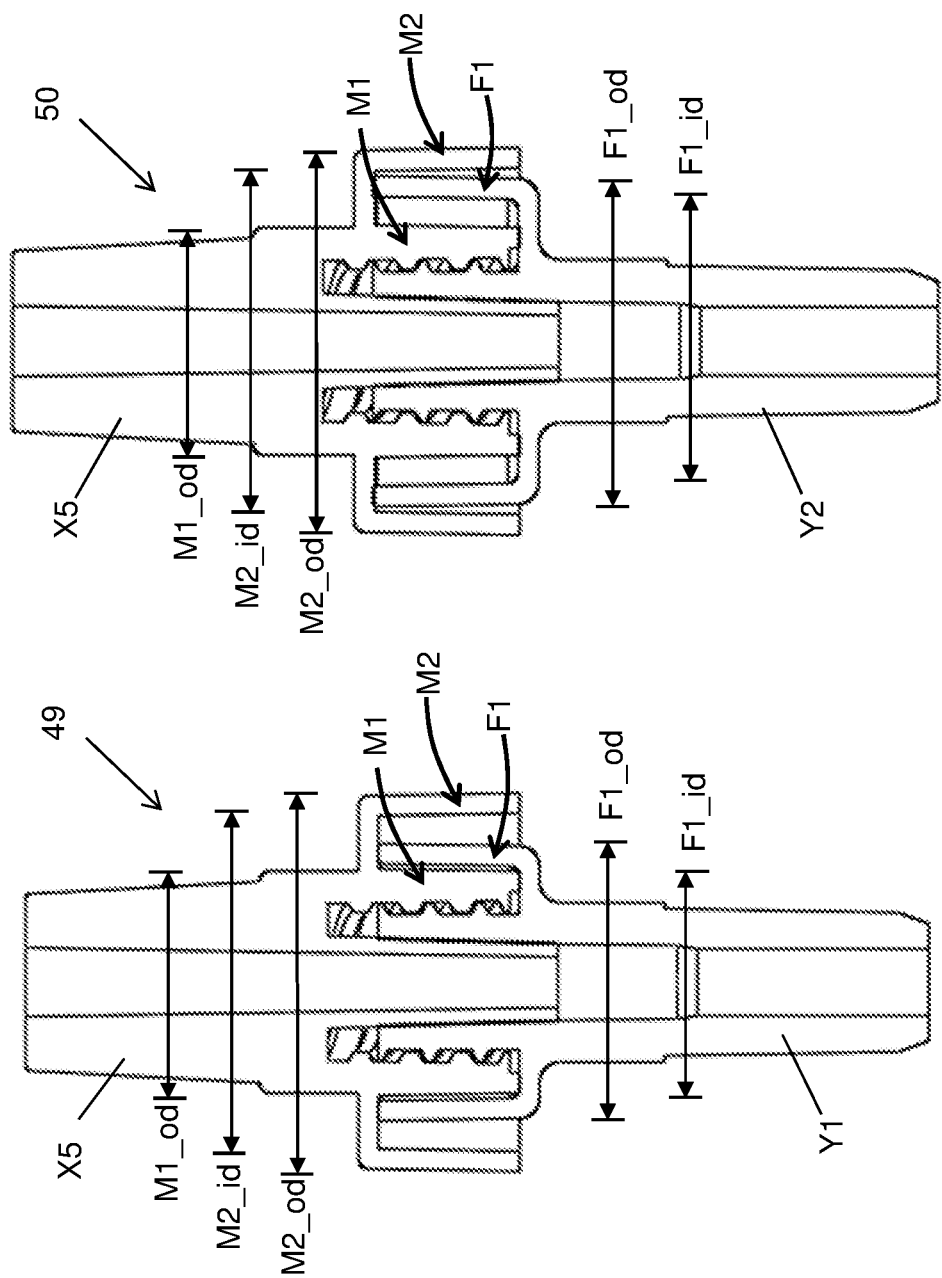

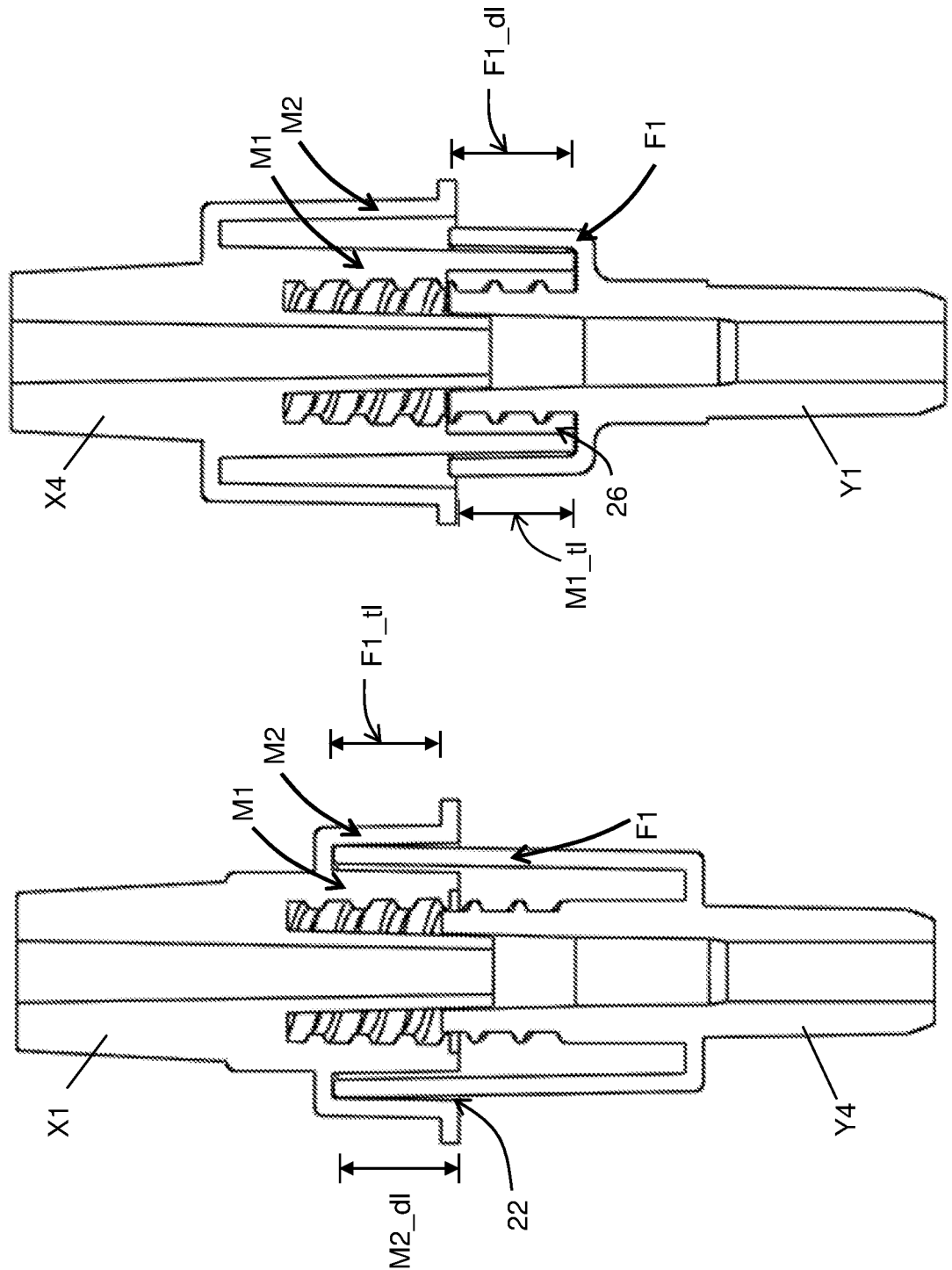

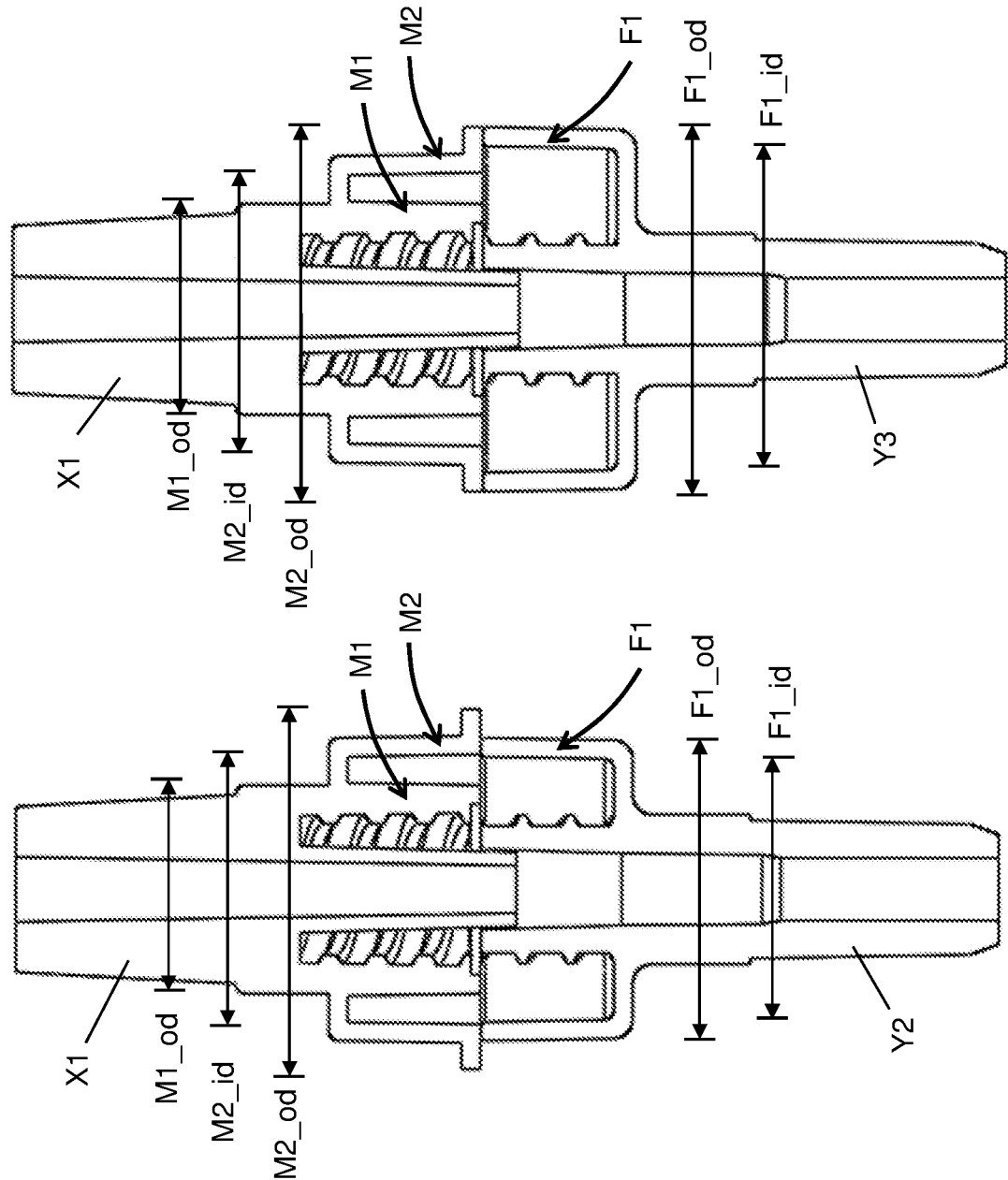

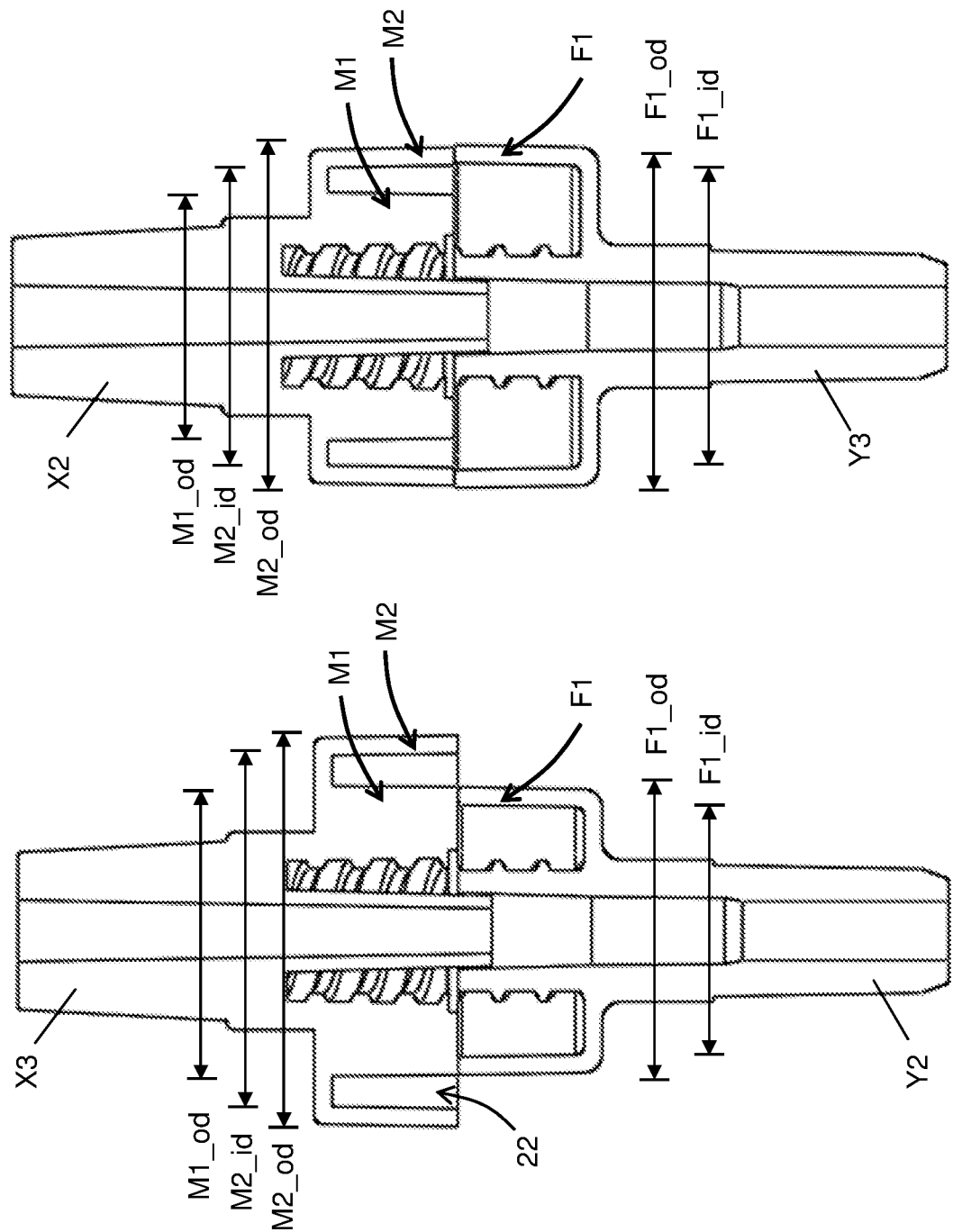

| X \ Y | YS | Y1 | Y1_Y4 | Y2 | Y2_Y4 | Y3 | Y3_Y4 |
|---|---|---|---|---|---|---|---|
| XS | + | + | + | + | + | + | + |
| X1 | + | + | o | o | o | o | o |
| X1_X4 | + | o | + | o | o | o | o |
| X2 | + | o | o | + | o | o | o |
| X2_X4 | + | o | o | o | + | o | o |
| X3 | + | o | o | o | o | + | o |
| X3_X4 | + | o | o | o | o | o | + |

FIG. 27

CONNECTOR SYSTEM WITH A FEMALE CONNECTOR AND A MALE CONNECTOR, AND A SYSTEM INCLUDING A PLURALITY OF THE CONNECTOR SYSTEMS

PRIORITY CLAIM

The present application is a National Phase of International Application No. PCT/EP2017/077231, filed Oct. 25, 2017, which claims priority to Swedish Application No. 1651392-1, filed Oct. 25, 2016, the entire contents of each of which are incorporated herein by reference and relied upon.

TECHNICAL FIELD

The present invention relates to the field of fluid connectors, and in particular connectors for medical applications such as connection of fluid lines and fluid bags in connection with blood treatment systems.

BACKGROUND

In medical applications it is common to use standardized connectors such as luer connectors according to ISO 594-1:1986, ISO 594-2:1998, ISO 80369-1:2010 or ISO/DIS 80369-7:2013, or connectors according to ISO 8637:2014 or ISO 8638:2014, where it is desired to connect two entities for transfer of fluid. A luer connection comprises an interconnecting female part and a male part, the male part being received as a friction fit within the female part, or by a lock fit accomplished by threads. Thanks to the standardized nature of the luer connector, products with such connectors will still fit together even if they have different manufacturers. However, as the connectors are widely used, they may be erroneously connected to the wrong device such as the wrong fluid bag, fluid line or syringe. A situation with an erroneously connected device may become life threatening, especially when medical care is brought to the patient's own home without continuous supervision from medical expertise, for example when using peritoneal dialysis (PD) or home hemodialysis (HD). Also in intensive care units the situation with critically ill patients and an overall stressful environment increases the risk of misconnection, for example when using CRRT (Continuous Renal Replacement Therapy).

To avoid making misconnections, it is common to for example color match the connector of a fluid line to an intended fluid bag with fluid to be delivered via the fluid line, together with careful instructions which fluid bag to be used. This solution has the drawback that it is still possible to make an erroneous connection as there is no structure stopping the engagement of the connectors.

A plurality of solutions to the problem have been disclosed where the connectors have been modified such that a modified female part will only fit with a thereto appropriately modified male part. From U.S. Pat. No. 5,947,937A a method and apparatus is known for preventing mismatching of blood types between a blood bag and a patient. A first and a second connector must have matching configuration coding in order to sealably connect and deliver blood to the patient, thereby preventing mismatch. From US2008/0287919A1 a luer-like non-standard medical fluid connector is known, that cannot be engaged with a standard luer fitting. The female and the male connectors are here modified to fit only with each other, the male connector is unable to receive a standard female luer fitting and the female connector is unable to engage with a standard male luer fitting.

From WO2012170961A1 a plurality of devices and systems for coupling of fluid lines are known. The devices and systems either have multiple connectors or a single non-round connector. The selectivity of the multiple connectors or single non-round connector requires a certain mutual orientation of the connectors in order to create a complete and non-leaking connection.

The above mentioned solutions delimit the use of such modified connector systems to certain applications.

SUMMARY

It is an objective of the disclosure to alleviate at least some of the drawbacks with the prior art. It is a further objective to provide a modified connector system that decrease the risk of misconnection of connectors of a system not intended to be interconnected. It is a further objective of the disclosure to provide a female connector and a male connector that are interconnectable to form a fluid tight connection, but are selective in which other connectors they are connectable with. It is a further objective to provide a connector system that is easy and cheap to manufacture. It is a still further objective to provide a connector system with as little modification as possible to an existing connector system. It is a further objective to provide an interconnectable modified female connector and a modified male connector that are still interconnectable to non-modified standard counterparts.

These objectives and others are at least partly achieved by the connector system and the system including a plurality of connector systems according to the independent claims, and by the embodiments according to the dependent claims.

According to one aspect, the disclosure relates to a connector system for a medical application. The connector system includes a male single channel fluid connector designed with an inner tube for passing of fluid, and a center collar with a threaded inner side and arranged concentric with the inner tube. The center collar is further defined by an outer diameter $M1\_od$. The connector system further includes a female single channel fluid connector designed with a tube for passing of fluid. The tube has a threaded outer side. The male single channel fluid connector is also designed with an outer collar arranged concentric with the inner tube outside the center collar. The outer collar is defined by an inner diameter $M2\_id$ and an outer diameter $M2\_od$ and a space in-between the center collar and the outer collar defining a depth stop. The space has an axial depth length $M2\_dl$. The center collar is optionally designed to have an axial top length $M1\_tl$ extending beyond the outer collar. The female single channel fluid connector is further designed with an outer collar arranged concentric with the tube and defined by an inner diameter $F1\_id$ and an outer diameter $F1\_od$, and a space in-between the tube and the outer collar defining a depth stop. The space has an axial depth length $F1\_dl$. The outer collar is optionally designed to have an axial top length $F1\_tl$ extending beyond the tube. Further are the outer diameter $M1\_od$, the inner diameter $M2\_id$, the inner diameter $M1\_id$ and the outer diameter $F1\_od$, the depth length $M2\_dl$, the depth length $F1\_dl$, the top length $M1\_tl$ and top length $F1\_tl$ designed such that the male single channel fluid connector is interconnectable both with: the female single channel fluid connector with the outer collar such that the outer collar is received inside the space, and with a luer type female single channel connector with a tube for passing of fluid having a threaded outer side with the same design and dimensions as the tube and a threaded outer side, as of the female single channel connector; and such that the female single channel fluid connector is interconnectable with a luer type male single channel connector with an inner tube for passing of fluid, and a center collar with a threaded inner side with the same design and dimensions as the inner tube and the threaded inner side as of the male single channel connector and to thereby form a fluid tight single channel connection for passage of fluid.

By the connector system, selectivity in interconnecting a connector to another connector is achieved. The connectors are still interconnectable with standard or predefined connectors, e.g. standard equivalent connectors that are not modified, as for example standard luer type e.g. luer lock connectors, and thus provide a security function by enabling interconnection with the luer type connector. Thereby it is still possible to connect and administer e.g. another fluid bag with the standard luer lock connector e.g. during emergency situations According to some embodiments, the inner diameter $F1\_id$ is greater than the outer diameter $M1\_od$, and the outer diameter $F1\_od$ is smaller than the inner diameter $M2\_id$.

According to some embodiments, the outer diameter $M1\_od$ is greater than a predefined outer diameter $M1\_ods$ of the luer type male single channel connector, and/or wherein the inner diameter $M2\_id$ is greater than a predefined dimension of the inner diameter $M2\_id$; and/or wherein the inner diameter $F1\_id$ is greater than a predefined dimension of the inner diameter $F1\_id$ and/or wherein the outer diameter $F1\_od$ is greater than a predefined dimension of the outer diameter $F1\_od$.

The above design requirements define terms for the diameters of the two connectors of a connection system when the two connectors are allowed to form a fluid tight single channel connection for passage of fluid between them. With a predefined dimension or equivalent is here meant e.g. a standard dimension or a scaled standard dimension of the standard connector in question. If there is no standard dimension, a predefined dimension is a property (length, diameter, etc.) that is the same for the system in question, e.g. a base dimension.

According to some embodiments, the outer diameter $M1\_od$ is extended by means of at least one protrusion. Thereby less material is needed than if the center collar had a uniform thickness, and costs can be saved.

According to some embodiments, the axial depth length $M2\_dl$ and the axial depth length $F1\_dl$ are equal within a margin, and the axial top length $M1\_tl$ and axial top length $F1\_tl$ are equal within a margin.

According to some embodiments, the luer type female single channel connector and the female single channel connector have a same predefined axial length $L\_ths$ of the thread on the outer side of the tube, respectively. Further, the axial top length $M1\_tl$ and the axial top length $F1\_tl$ are equal to the predefined axial length $L\_ths$ of the thread within a margin, respectively. Also, the axial depth length $M2\_dl$ and the axial depth length $F1\_dl$ are equal to twice the predefined axial length $L\_ths$ of the thread within a margin, respectively.

The above design requirements define terms for the axial top lengths and the axial depth lengths of the two connectors of a connection system when the two connectors are allowed to form a fluid tight single channel connection for passage of fluid between them.

According to a second aspect, the disclosure relates to a system including a plurality of connector systems as explained herein. In the system, the interconnectable male single channel fluid connector and female single channel fluid connector of each connector system are designed to be non-interconnectable with any of the male single channel fluid connector and female single channel connector of the other connector systems of the plurality of connector systems. Further, the luer type female single channel connector, the luer type male single channel connector and any certain predefined dimension are the same for all the plurality of connector systems of the system.

By such a system, selectivity in interconnection is achieved to thereby avoid misconnection of connectors.

According to some embodiments, the plurality of connector systems includes a connector system where the axial top length $F1\_tl$ of the female single channel fluid connector is greater or equal to the axial depth length $M2\_dl$ of any male single channel fluid connector of the other connector systems of the plurality of connector systems. Further the luer type female single channel connector and the female single channel connector have a same predefined axial length $L\_ths$ of the thread on the outer side of the tube, respectively, and wherein the axial top length $F1\_tl$ is equal to the predefined axial length of the thread within a margin.

According to some embodiments, the plurality of connector systems includes a connector system where the top length $M1\_tl$ of the male single channel fluid connector is greater or equal to the depth length $F1\_dl$ of any female single channel fluid connector of the other connector systems of the plurality of connector systems. Further, the luer type female single channel connector and the female single channel connector have a same predefined axial length $L\_ths$ of the thread on the outer side of the tube, respectively. Also, the axial depth length $F1\_dl$ is equal to the predefined axial length $L\_ths$ of the thread within a margin.

The above design requirements define terms for the axial top lengths and the axial depth lengths of two connectors from different connection systems when the two connectors are prevented to engage and to form a fluid tight single channel connection for passage of fluid between them.

According to some embodiments, the plurality of connector systems includes a connector system where the inner diameter $F1\_id$ of the female single channel fluid connector is less than the outer diameter $M1\_od$ of any male single channel fluid connector of the other connector systems of the plurality of connector systems, or wherein the outer diameter $F1\_od$ of the female single channel fluid connector is greater than the inner diameter $M2\_id$ of any male single channel fluid connector of the other connector systems of the plurality of connector systems. Also, the inner diameter $F1\_id$ of the female single channel fluid connector is less than the outer diameter $M2\_od$ of any male single channel fluid connector of the other connector systems of the plurality of connector systems.

The above design requirements define terms for the diameters of two connectors of different connection systems when the two connectors are prevented to engage and to form a fluid tight single channel connection for passage of fluid between them.

According to a third aspect, the system includes a plurality of connector systems wherein each connector system includes a modified male luer lock fluid connector X and a thereto interconnectable modified female luer lock fluid connector Y. The interconnectable modified male luer lock fluid connector X and modified female luer lock fluid connector Y of each connector system are designed to be non-interconnectable with any of the modified male luer lock fluid connectors X and modified female luer lock fluid connectors Y of the other connector systems of the plurality of connector systems. The modified male luer lock fluid connectors X are further interconnectable to a same standard female luer lock fluid connector YS, and the modified female luer lock fluid connectors Y are interconnectable to a same standard male luer lock fluid connector XS.

The third aspect presents a specific system based on luer lock connectors.

The herein disclosed connectors are single channel fluid connectors meaning that each connector is only arranged with one single channel for passing fluid. A male single channel fluid connector may be referred to as a male connector, or a connector X. A female single channel fluid connector may be referred to as a female connector, or a connector Y. When the male connector and the female connector are interconnected, their respective single channel match each other such that a fluid tight connection or fitting is achieved with one common channel and fluid can only be passed in the connection via the common channel. No other channels are present in the connectors. The single channels are further preferably located centered in the connectors. Thus, the single channel of the male connector is located centered in the same connector. Further, the single channel of the female connector is located centered in the same connector.

The centered single channels allow rotational engagement of the connectors. Rotational engagement here generally means that while the male single channel fluid connector is inserted into the female single channel fluid connector to form a fluid tight connection, any of the engaging parts of the connectors is rotated in relation to the other engaging part of the other connector of the connector system.

BRIEF DESCRIPTION OF THE DRAWINGS

FIG. 1 illustrates a standard male luer connector with a lock tip.

FIG. 2 illustrates a standard female luer connector configured to receive the male luer connector with a lock tip in FIG. 1.

FIG. 3 illustrates the standard male luer connector in FIG. 1 connected to the standard female luer connector in FIG. 2.

FIG. 4 illustrates a modified standard male luer connector according to some embodiments.

FIGS. 5-6 illustrate examples of the modified standard male luer connector in FIG. 4 where the diameters have been modified.

FIGS. 14-17 illustrate connector systems according to some embodiments.

FIGS. 18-25 illustrate modified standard male luer connectors and modified standard female luer connectors which do not fit together.

FIG. 27 is illustrating a connectivity chart of a system according to some embodiments.

DETAILED DESCRIPTION

Figure 8:
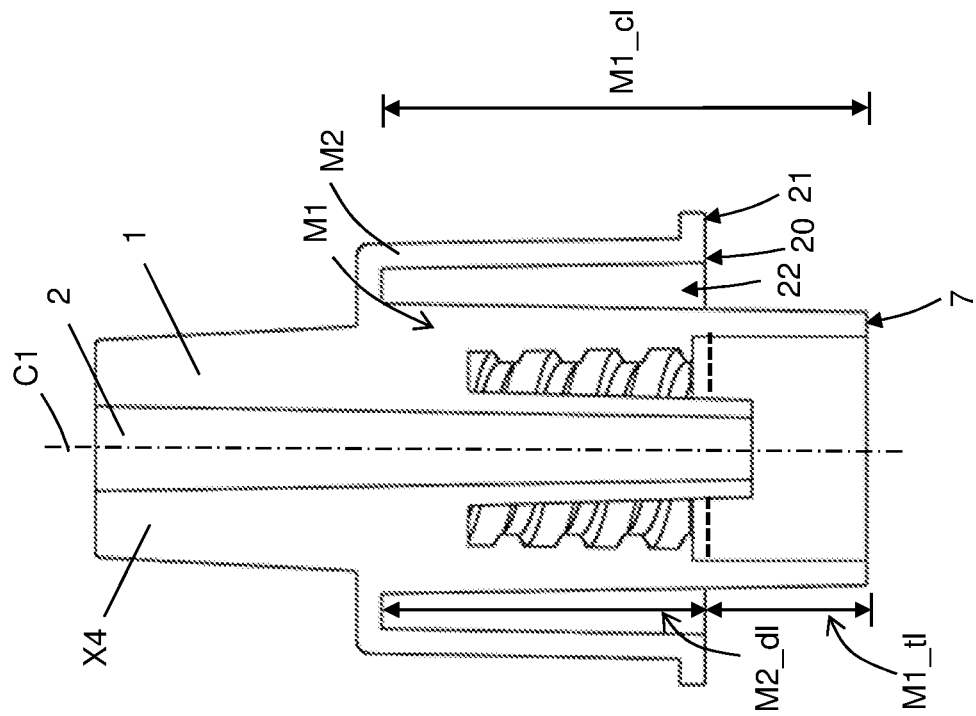
FIG. 8 illustrates an example of the modified standard male luer connector in FIGS. 4 and 7 where the axial lengths have been modified.
Figure 7:
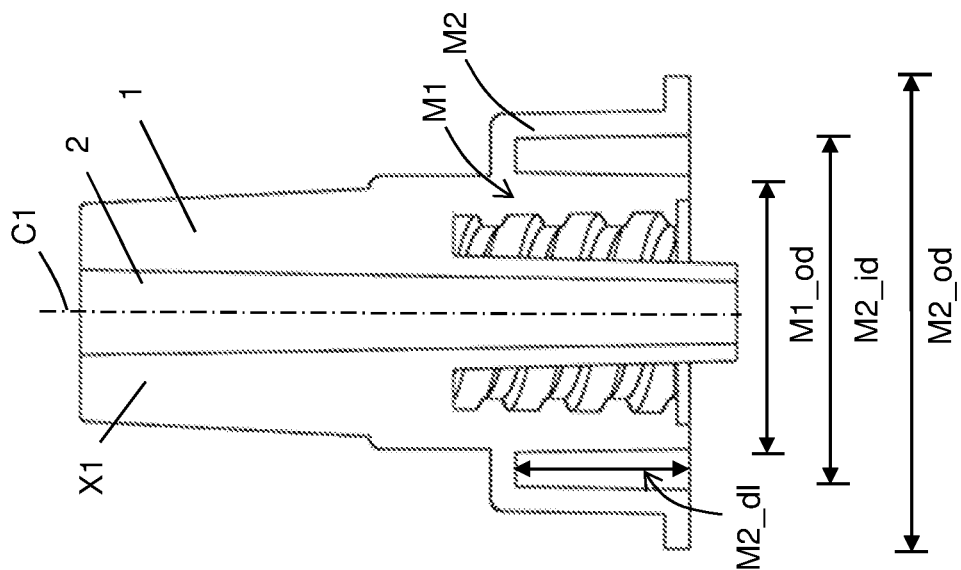
FIG. 7 illustrates the modified standard male luer connector of FIG. 4.

In the following connector systems will be described, where each connector system includes a modified female connector and a thereto interconnectable modified male connector. The modified female connector may be a modified female luer lock fluid connector, and the modified male connector may be a modified male luer lock fluid connector. The modified female connector and the modified male connector have been modified in relation to standardized, i.e. predefined, equivalents as will be described in the following. Examples of standardized luer type connectors such as luer lock connectors are explained e.g. in ISO 594-1:1986, ISO 594-2:1998, ISO 80369-1:2010 or ISO/DIS 80369-7:2013, or connectors according to ISO 8637: 2014 or ISO 8638:2014. The luer type connectors may also be referred to as conical fittings of luer type. Also, a system including a plurality of the connector systems, where the modified female connector and the corresponding modified male connector of a connector system are non-interconnectable to any of the other modified female connectors and corresponding modified male connectors of the other connector systems, will be explained. The connectors are here mainly illustrated in isolation as male connectors and female connectors, but may instead be connected to for example a syringe barrel, a needle, a fluid line or a fluid bag. The connectors described herein may e.g. be made of plastic or metal. All the connectors herein are fluid connectors, and in particular single channel fluid connectors. With "interconnectable" is here meant connectors, e.g. a female connector and a male connector, that are designed such that they can be connected together, or engaged, to form a fluid tight, detachable, connection or coupling for transfer of fluid. With "non-interconnectable" is here meant connectors, e.g. a female connector and a male connector, that have geometries or other design characteristics that prevent engagement of the connectors such that no fluid tight connection can be achieved, in order to prevent unintended connections. Thus, such connectors are not connectable and cannot be engaged with each other.

FIG. 1 illustrates a prior known standardized male single channel connector XS with a lock tip, here a standard male luer lock connector. FIG. 2 illustrates a standardized female single channel connector YS, here a standard female luer lock connector, configured to receive the male single channel connector XS in FIG. 1. A lock tip is further defined as a male connector arranged with one or several threads mating with corresponding threads on a female connector, such that a fluid tight fitting can be created between them by screwing them together. FIG. 3 illustrates the standard male single channel connector XS in FIG. 1 interconnected with the standard female single channel connector YS in FIG. 2. When connected, they form a fluid tight connection or fluid tight fitting. The connectors XS, YS may be referred to as conical fittings of luer type, standard luer lock connectors, or male and female standard 6% (Luer) lock conical fittings.

The standardized male single channel connector XS in FIG. 1, hereinafter referred to as the connector XS, has a male connector body 1 defining an inner tube 2 for passing of fluid, and defining a center collar M1. The connector XS is arranged for receiving a standardized female luer connector YS at one end 3, and for connection e.g. to a fluid line or a fluid bag at the other end 4. The inner tube 5, or nozzle, defines a single fluid channel 2 for passing of fluid. The inner tube 5 further defines an axis C1. The inner tube 5 has a standard inner diameter XS_ids. The inner tube 5 further has a standard outer diameter XS_ods. In some embodiments, the inner tube 5 has a tapered outer shape of a cone. The cone has for example a 6% taper. The standard outer diameter XS_ods of the inner tube 5 then increases from its most distal end and inwards. The center collar M1 has a threaded inner side 6 arranged concentric with the inner tube 5. The thread 9 on the threaded inner side 6 is thus an inner thread. In some embodiments, the thread 9 is separated into two separate threads, such that the threads may be engaged by the threaded outside 14 of the female connector 13 at different opposite locations of the inside 6 of the center collar M1. Such a construction with separated threads is referred to as a double thread. The center collar M1 is further joined at one end to the inner tube 5. The center collar M1 has a center collar face 7 at the other end being perpendicular to the axis C. The center collar face 7, and thus the center collar M1, is defined by a standard outer diameter M1_ods. The diameter M1_ods is also referred to as a predefined outer diameter of the connector XS. The standard outer diameter M1_od defines an outer limitation of the standardized male connector XS. In some embodiments, the inner tube 5 extends beyond the center collar face 7. The inner tube 5 the projects from the center collar M1 with a projection distance P. In other embodiments, the inner tube 5 ends in height with the face 7. Between the inner tube 5 and the center collar M1 a space 8 is defined. The space 8 is designed to receive a corresponding standard single channel female connector YS illustrated in FIG. 2. The connector XS is here illustrated with a permanently connected inner thread center collar M1. Instead, the connector X3 may have a rotatable internally threaded center collar (not shown).

The standard female single channel connector YS in FIG. 2, hereinafter referred to as the connector YS, is arranged for receiving the standardized male luer connector XS at one end 10, and for connection e.g. to a fluid line or a fluid bag at the other end 11. The connector YS includes a female connector body 12. The female connector body 12 defines a tube 13 for passing of fluid. The tube 13 is designed to receive the inner tube 5 of the connector XS, and defines a single fluid channel 16 for passing of fluid. The tube 13 further defines an axis C2. The tube 13 has a face 17 at the end 10 of the connector YS designed to receive the connector XS. The face 17 is being perpendicular to the axis C2. The tube 13 has a standard inner diameter YS_ids. The inside of the tube 13 may have a tapered shape mating with a tapered shape of the outer side of the inner tube 5. For example, the inside of the tube 13 has a 6% taper. The standard inner diameter YS_ids of the tube 13 then decreases from its most distal end, i.e. the face 17, and inwards. The tube 13 further has a standard outer diameter YS_ods. The tube 13 has a threaded outer side 14. The tread 15 on the threaded outer side 14 is thus an outer thread. The thread 15 has an axial length L_ths being coaxial with the axis C2. The thread 15 of the connector YS mate with the thread 9 on the connector XS.

In FIG. 3 the connector XS and the connector YS are illustrated when they are connected, or fitted, together and forms a fluid tight connection. The connector XS and the connector YS have been connected by screwing them together as a screw joint, including a turning as well as a sliding motion between the connector XS and the connector YS. When the inner tube 5 is received inside the tube 13, the inner side of the tube 13 fits snuggly with the outer side of the inner tube 5. Because of the tapered shapes and the screw joint, the connector YS is locked in place to the connector XS and thus a lock fit is accomplished. The fluid tight connection is held in place by friction acting between the inner side of the tube 13 and the outer side of the tube 5, and between the inner thread 9 and the outer thread 15.

In FIGS. 4-8 a plurality of male single channel fluid connectors X are illustrated, and in the FIGS. 9-13 a plurality of female single channel fluid connectors Y are illustrated, and that will be explained in the following. Thereafter, a plurality of connector systems according to the first aspect and illustrated in FIGS. 14-17 will be explained, each connector system including one of the male single channel fluid connectors X of FIGS. 4-8, and a thereto interconnected corresponding female single channel fluid connector Y from one of the FIGS. 9-13. Thereafter, some of the plurality of male single channel fluid connectors X of the FIGS. 4-8 and some of the plurality of female single channel fluid connectors Y of the FIGS. 9-13 are illustrated when they not mate, thus they are non-interconnectable. Thereafter the second aspect will be explained, with reference to some or all of the plurality of male single channel fluid connectors X and the plurality of female single channel fluid connectors Y explained herein. According to the second aspect, a system is proposed that includes a plurality of the connector systems with a male single channel fluid connector X and a thereto interconnectable female single channel fluid connector Y, that are non-interconnectable with any of the other connectors X, Y of the plurality of connector systems. All of the male single channel fluid connectors X are however interconnectable with the previously described connector YS to form a fluid tight connection, and all of the female single channel fluid connectors Y are interconnectable with the previously described connector XS to form a fluid tight connection.

The male single channel fluid connectors X1-X4 in the FIGS. 4-8 are commonly referred to as the "connectors X". The connectors X are modified in respect of the connector XS of FIG. 1. However, they are all still connectable to the connector YS of FIG. 2. The connectors X all have in common with the connector XS of FIG. 1 that they also each is designed with a male connector body 1, a single fluid channel 2, one end 3 designed for receiving a female connector, one opposite end 4 designed to be connected to a fluid line or a fluid bag, an inner tube 5, a center collar M1, a threaded inner side 6 of the center collar M1 with a thread 9, and a space 8 between the inner tube 5 and the center collar M1, with substantially the same dimensions as the connector YS. The connectors X are however all modified in respect of the connector XS in that they are designed with a respective outer collar M2 arranged concentric with the inner tube 5 outside the center collar M1. Thus, the male connector body 1 defines the outer collar M2. The outer collar M2 is at one end, i.e. a proximal end, arranged to an outer side 18 of the center collar M1 via a projecting part 19 projecting radially from the outer side 18 of the center collar M1 or inner tube 5 with respect to the axis C1. At the other end of the outer collar M2, thus at the distal end of the outer collar M2, an outer collar face 20 is defined. The outer collar face 20 is parallel with the center collar face 7. The outer collar M2, thus the outer collar face 20, is defined by an inner diameter M2_id and an outer diameter M2_od. The connector X is further defining a space 22 in-between the center collar M1 and the outer collar M2 defining a depth stop. The space 22 has an axial depth length M2_dl. The axial depth length M2_dl extends from the outer collar face 20 to a depth stop face or end, thus an inner radial stop of the space 22. The outer collar M2, the projecting part 19 and the tube 5 are all integrated parts of the male connector body 1 and thus of a connector X. The outer collar M2 is in some embodiments arranged with a flange 21.

In FIG. 4 the connector X1 is illustrated according to a first embodiment of the connectors X. The connector X1 corresponds to the connector XS with the difference that it is designed with the outer collar M2. More in particular, the diameter M1_od of the connector X1 equals the diameter M1_ods (FIG. 1). Further, the inner diameter M2_id equals a base diameter K2, and the outer diameter M2_od equals a base diameter K3. The axial depth length M2_dl equals the thread length L_ths (FIG. 2). The center collar M1 has an axial length M1_cl from a depth stop end or face of the space 22 to the center collar face 7. The connector X1 is in this example designed with an axial length M1_cl that is equal to the axial depth length M2_dl, thus L_ths. According to some embodiments, the dimensions of the connector X1 are thus base dimensions for the other remaining connectors of the connectors X. A base diameter is e.g. here defined to be a starting diameter from which a diameter of a connector is increased. A base diameter may be the predefined diameter.

In FIG. 5 the connector X2 is illustrated according to a second embodiment of the connectors X. The connector X2 corresponds to the connector X1 of FIG. 4, except that some diameters have been modified. More in particular, the diameter M1_od of the connector X2 is greater than the diameter M1_ods with a distance ΔK1. Further, the inner diameter M2_id is greater than the base diameter K2 with a distance ΔK22, and the outer diameter M2_od is greater than the base diameter K3 with a distance ΔK33. The axial depth length M2_dl equals the thread length L_ths (FIG. 2) within a margin.

In FIG. 6 the connector X3 is illustrated according to a third embodiment of the connectors X. The connector X3 corresponds to the connector X1 and X2 of FIGS. 4 and 5, except that the diameters have been further modified. More in particular, the diameter M1_od of the connector X3 is greater than the diameter M1_ods with a distance ΔK1+ΔK11. Further, the inner diameter M2_id is greater than the base diameter K2 with a distance ΔK22+ΔK222, and the outer diameter M2_od is here greater than the base diameter K3 with a distance ΔK33+ΔK333. Also in this embodiment, the axial depth length M2_dl equals the thread length L_ths (FIG. 2) within a margin.

FIG. 7 is again illustrating the connector X1 of FIG. 4 to be able to closely compare it with the connector X4 of FIG. 8. In FIG. 8 the connector X4 is illustrated according to a fourth embodiment of the connectors X. The connector X4 corresponds to the connector X1 of FIG. 4 and thus FIG. 7, except that the center collar M1 in the fourth embodiment further is designed to have an axial top length M1_tl extending beyond the outer collar M2, thus extending from and beyond the outer collar face 20, and in having a depth length M2_dl that is greater than the depth length of the connector X1. In this fourth embodiment, the axial top length M1_tl equals the thread length L_ths (FIG. 2) within a margin. Further, the depth length M2_dl is twice the thread length L_ths (FIG. 2) within a margin. The axial outer length M1_cl of the inner collar is then three times the thread length L_ths (FIG. 2), thus the top length M1_tl plus the depth length M2_dl, within a margin. The outer collar M2 is here provided with a flange 21. The fourth embodiment is also referred to as a connector X1_X4, as it has the same diameters as the connector X1 and the same lengths as the connector X4.

The center collar M1 thus has the axial length M1_cl extending from a depth stop end or face limiting the space 22, to the center collar face 7. The connector X1 is in this example designed with an axial length M1_cl that is equal to the axial depth length M2_dl, thus equal to L_ths.

According to a fifth embodiment of the connectors X, the connector X2 of FIG. 5 is designed with the axial top length M1_tl, as of the connector X4, extending beyond the outer collar M2, thus extending from and beyond the outer collar face 20, and in having a depth length M2_dl, as of connector X4, that is greater than the depth length of the connector X1. The dimensions of the axial top length M1_tl, the depth length M2_dl and the axial outer length M1_cl are the same as for the connector X4. The fifth embodiment is also referred to as a connector X2_X4, as it has the same diameters as the connector X2 and the same lengths as the connector X4.

According to a sixth embodiment of the connectors X, the connector X3 of FIG. 6 is designed with the axial top length M1_tl, as of the connector X4, extending beyond the outer collar M2, thus extending from and beyond the outer collar face 20, and in having a depth length M2_dl, as of connector X4, that is greater than the depth length of the connector X1. The dimensions of the axial top length M1_tl, the depth length M2_dl and the axial outer length M1_cl are the same as for the connector X4. The sixth embodiment is also referred to as a connector X3_X4, as it has the same diameters as the connector X3 and the same lengths as the connector X4.

The female single channel fluid connectors Y1-Y4 in the FIGS. 9-13 are commonly referred to as the "connectors Y". The connectors Y are modified in respect of the connector YS of FIG. 2. However, they are all still connectable to the connector XS of FIG. 1. The connectors Y all have in common with the connector YS of FIG. 2 that they also each have a female connector body 12, a single fluid channel 16, one end 10 designed for receiving a male connector, one opposite end 11 designed to be connected to a fluid line or a fluid bag, a tube 13, and a threaded outer side 14 of the tube 13 with a thread 15, with substantially the same dimensions as the connector YS. Further, all the connectors Y have a same thread length L_th of the thread 15 equal to the predefined axial length L_ths of the thread 15 of the connector YS. The connectors Y are however all modified in respect of the connector YS in that they are designed with a respective outer collar F1 arranged concentric with the tube 13, and arranged outside the tube 13. Thus, the female connector body 12 defines the outer collar F1. The outer collar F1 is at one end arranged to an outer side 23 of the tube 13 via a projecting part 24 projecting radially from the outer side 23 of the tube 13 with respect to the axis C2. At the other end of the outer collar F1, thus at the distal end of the outer collar F1, an outer collar face 25 is defined. The outer collar face 25 is parallel with the tube face 17. The outer collar F1, thus the outer collar face 25, is defined by an inner diameter F1_id and an outer diameter F1_od. The connector Y is further defining a space 26 in-between the tube 13 and the outer collar F1 defining a depth stop. The space 26 has an axial depth length F1_dl. The outer collar F1, the projecting part 24 and the tube 13 are all integrated parts of the female connector body 12 and thus of a connector Y.

Figure 9:
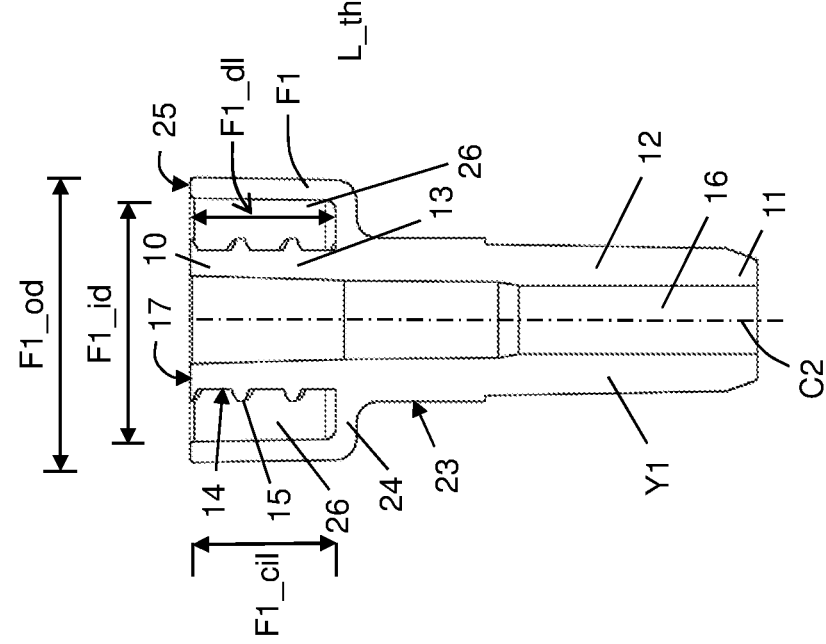
FIG. 9 illustrates a modified standard female luer connector according to some embodiments.

In FIG. 9 the connector Y1 is illustrated according to a first embodiment of the connectors Y. The connector Y1 corresponds to the connector YS with the difference that it is designed with the outer collar F1. More in particular, the inner diameter F1_id equals a base diameter D1, and the outer diameter F1_od equals a base diameter D2. The thread 15 has a thread length L_th that equals the thread length L_ths of the connector Y. Also, the axial depth length F1_dl equals the thread length L_ths of the connector YS within a margin. The outer collar F1 has an axial inner length F1_cil from a depth stop end of the depth stop to the outer collar face 25. The connector Y1 is in this example designed with an axial length F1_cil that is equal to the axial depth length F1_dl, and thus equal to L_ths. A base diameter is here defined to be a starting diameter from which a diameter of a connector is increased.

Figure 10:
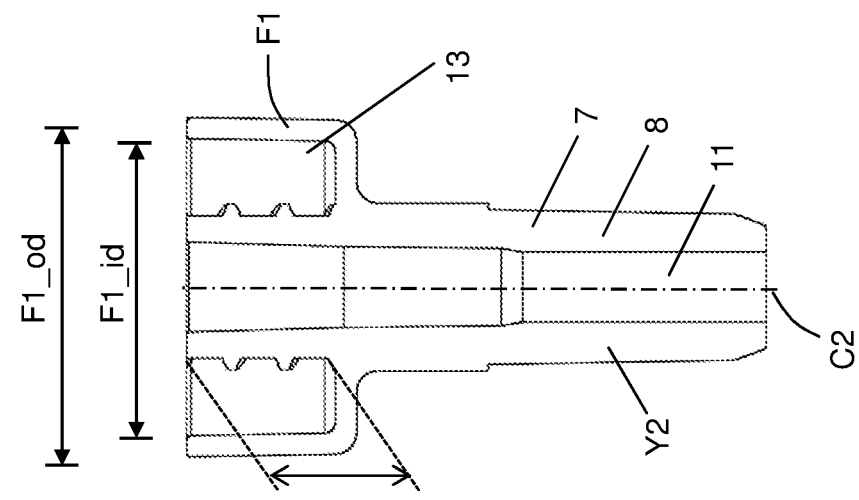

In FIG. 10 the connector Y2 is illustrated according to a second embodiment of the connectors Y. The connector Y2 corresponds to the connector Y1 of FIG. 7, except that some diameters have been modified. More in particular, the diameter F1_id of the connector Y2 is greater than the base diameter D1 with a distance ΔD11. Further, the inner diameter F1_od is greater than the base diameter D2 with a distance ΔD22. The axial depth length F1_dl equals the thread length L_ths (FIG. 2) within a margin.

Figure 11:
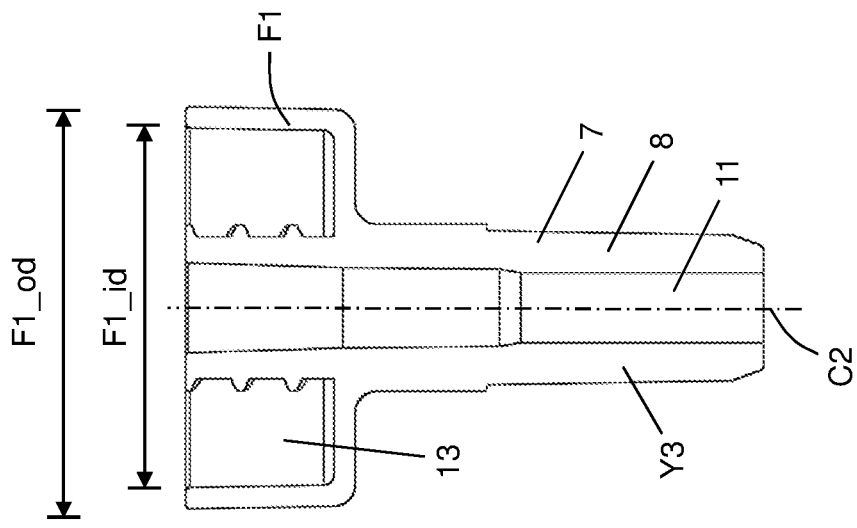
FIGS. 10-11 illustrate examples of the modified standard female luer connector in FIG. 9 where diameters have been modified.

In FIG. 11 the connector Y3 is illustrated according to a third embodiment of the connectors Y. The connector Y3 corresponds to the connector Y1 and Y2 of FIGS. 9 and 10, except some of the diameters have been further modified. More in particular, the inner diameter F1_id of the connector Y3 is greater than the diameter D1 with a distance ΔD11+ΔD111. Further, the outer diameter F1_od is greater than the diameter D2 with a distance ΔD22+ΔD222. Also in this embodiment, the axial depth length F1_dl equals the thread length L_ths (FIG. 2) within a margin.

Figure 13:
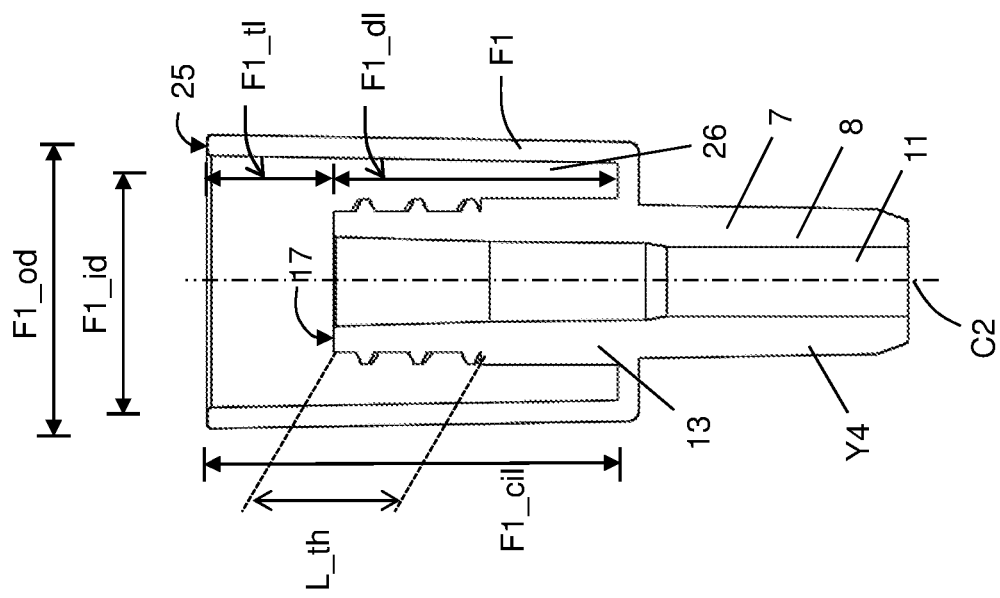
FIG. 13 illustrates an example of the modified standard male luer connector in FIGS. 9 and 12 where the axial lengths have been modified.
Figure 12:
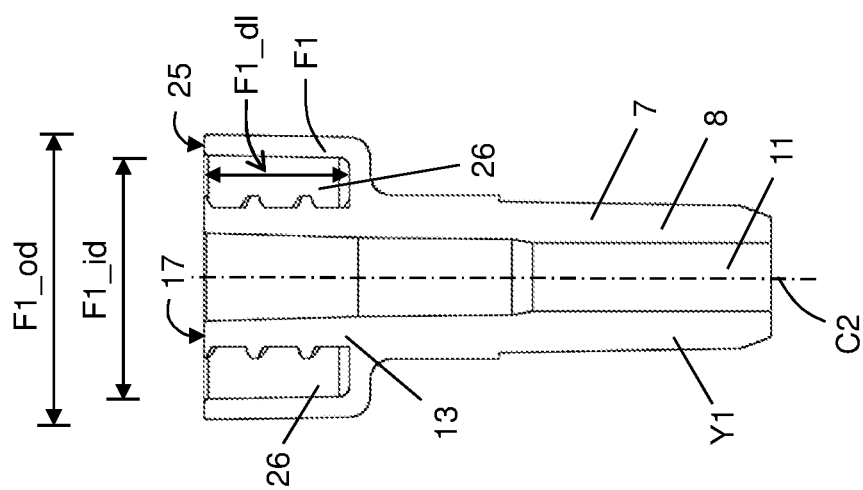
FIG. 12 illustrates the modified standard female luer connector of FIG. 9.

FIG. 12 is illustrating the connector Y1 of FIG. 9 to be able to closely compare it with the connector Y4 of FIG. 13. In FIG. 13 the connector Y4 is illustrated according to a fourth embodiment of the connectors Y. The connector Y4 corresponds to the connector Y1 of FIGS. 9 and 12, except that the outer collar F1 in the fourth embodiment further is designed to have an axial top length F1_tl extending beyond the tube 13, in other words, beyond the tube face 17 in a distal direction, and in having a depth length F1_dl that is greater than the depth length of the connector Y1. In this third embodiment the axial top length F1_tl equals the thread length L_ths (FIG. 2) within a margin. Further, the depth length F1_dl is twice the thread length L_ths (FIG. 2) within a margin. The axial inner length F1_cil of the outer collar F1 then is three times the thread length L_ths (FIG. 2), thus the top length F1_tl plus the depth length F1_dl, within a margin. In the first, second and third embodiments illustrated in FIGS. 9-12, the axial top length F1_tl extending beyond the tube 13 is zero, or essentially zero. The fourth embodiment of the connector Y is also referred to as a connector Y1_Y4, as it has the same diameters as the connector Y1 and the same lengths as the connector Y4.

According to a fifth embodiment of the connectors Y, the connector Y2 of FIG. 10 is designed with the outer collar F1 having an axial top length F1_tl extending beyond the tube 13, in other words, beyond the tube face 17 in a distal direction, as of the connector Y4, and is further designed with a depth length F1_dl that is greater than the depth length of the connector Y1, as of the connector Y4. The dimensions of the axial top length F1_tl, the depth length F1_dl and the axial inner length F1_cil of the outer collar F1 are the same as for the connector Y4. The fifth embodiment is also referred to as a connector Y2_Y4, as it has the same diameters as the connector Y2 and the same lengths as the connector Y4, which have been previously described.

According to a sixth embodiment of the connectors Y, the connector Y3 of FIG. 11 is designed with the outer collar F1 having an axial top length F1_tl extending beyond the tube 13, in other words, beyond the tube face 17 in a distal direction, as of the connector Y4, and is further designed with a depth length F1_dl that is greater than the depth length of the connector Y1, as of the connector Y4. The dimensions of the axial top length F1_tl, the depth length F1_dl and the axial inner length F1_cil of the outer collar F1 are the same as for the connector Y4. The sixth embodiment is also referred to as a connector Y3_Y4, as it has the same diameters as the connector Y3 and the same lengths as the connector Y4, which have been previously described.

The above described connectors X are designed to mate with a respective connector Y of the connectors Y, to form a fluid tight connection. Each mating connector X and connector Y forms a connector system. The described connectors X are respectively designed with an outer diameter M1_od, an inner diameter M2_id, an outer diameter M2_od, a depth length M2_dl and a top length M1_tl, and the described connectors Y are respectively designed with an outer diameter F1_od, a depth length F1_dl and a top length F1_tl, such that a respective connector X1, X2, X3, X4 of the connectors X is interconnectable both with a respective connector Y1, Y2, Y3, Y4 of the connectors Y such that the outer collar F1 is received inside the space 12, and with a luer type, i.e. predefined, female single channel connector, e.g. the connector YS, such that the connector Y also is interconnectable with a luer type, i.e. predefined, male single channel connector, e.g. the connector XS, and to thereby form a fluid tight single channel connection for passage of fluid.

The luer type or predefined female single channel connector is thus for example the standardized connector YS (FIG. 2), e.g. a standard female luer lock connector. The luer type or predefined female single channel connector may be another kind of connector, e.g. with a scaled size (greater or smaller) than demanded for a standardized connector YS. The predefined female single channel connector is designed with a tube 13 for passing of fluid having a threaded outer side 14 with the same design and dimension as the tube 13 and threaded outer side 14 as of the female single channel connector Y. The predefined female single channel connector is thus for example the standardized connector XS (FIG. 1). The predefined male single channel connector is designed with an inner tube 5 for passing of fluid, and a center collar M1 with a threaded inner side 6 with the same design and dimension as the inner tube 5 and the threaded inner side 6 as of the male single channel connector X. The predefined male single channel connector is thus for example the standardized connector XS (FIG. 1), e.g. a standard male luer lock connector. The predefined male single channel connector may however be another kind of connector, e.g. with a scaled size (greater or smaller) than demanded for a standardized connector XS.

Figure 15:
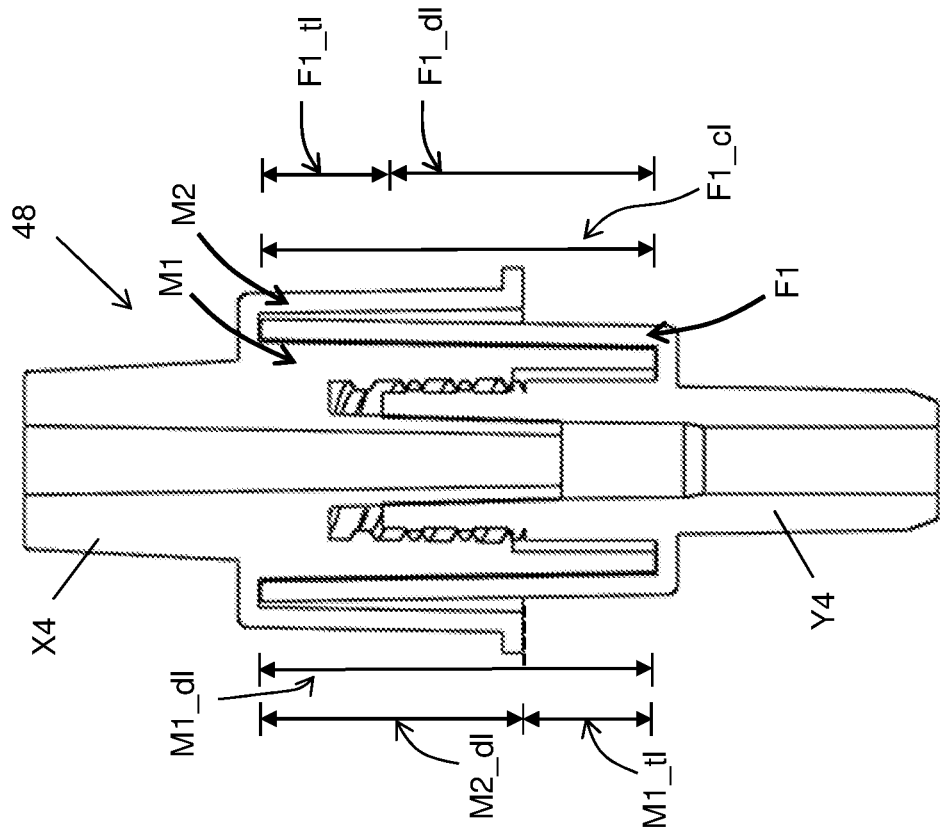
Figure 14:
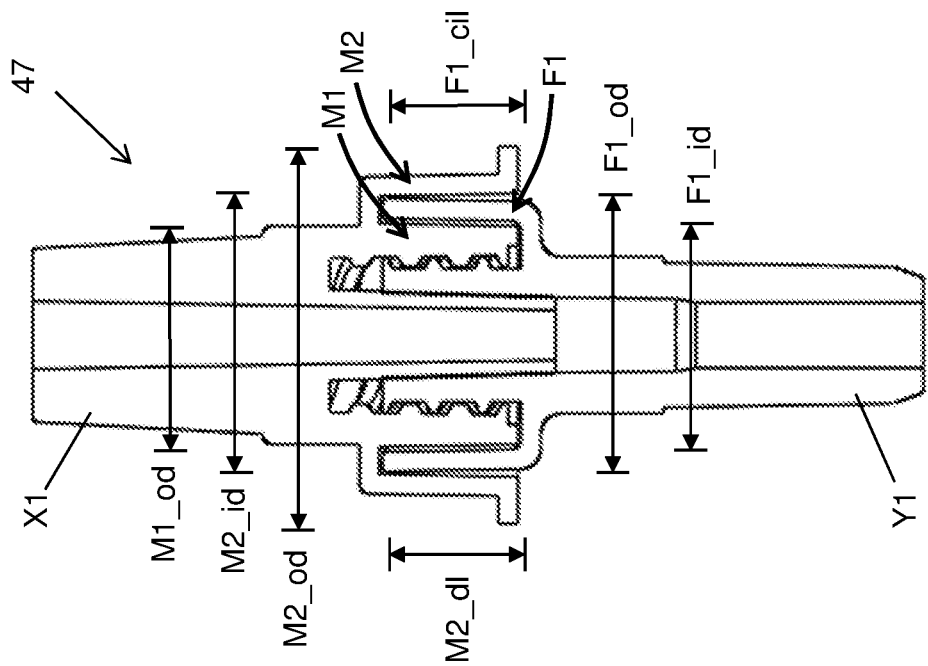

The FIGS. 14 to 16 illustrates such connector systems and the connector systems will now be described with reference to these figures. A prerequisite for each herein described connector system is that the inner diameter F1_id of the female connector is greater than the outer diameter M1_od of the corresponding male connector, and that the outer diameter F1_od of the same female connector is smaller than the inner diameter M2_id of the male connector.

In FIG. 14 a connector system 47 according to a first embodiment is illustrated. The connector system 47 is in some embodiments referred to as a base connector system 47, as the dimensions of the diameters and lengths provide a base from which diameters and lengths of other connector systems with interconnectable connectors are modified, that is, increased. Thus, a base diameter may be referred to as a predefined diameter, and a base length may be referred to as a predefined length. The connector system 47 includes the connector X1 of FIG. 4, and the connector Y1 of FIG. 9. The requirements for the design of the connector system 47 of FIG. 14 includes that the inner diameter F1_id of the connector Y1 is greater than the outer diameter M1_od of the connector X1, and that the outer diameter F1_od of the connector Y1 is smaller than the inner diameter M2_id of the connector X1. Further, the depth stop length M1_dl is equal to the inner length F1_cil of the outer collar F1, and further equal to the thread length L_ths (FIG. 2). Here, this is accomplished as D1 is greater than M1_ods, and D2 is smaller than K2. A further requirement for the design of the connector system 47 is that the axial top length M1_tl and axial top length F1_tl both are essentially zero.

A connector system 45 (FIG. 26) according to a second embodiment is accomplished by the connector X2 of FIG. 5 and the connector Y2 of FIG. 10. Further, a connector system 46 (FIG. 26) according to a third embodiment is accomplished by the connector X3 of FIG. 6 and the connector Y3 of FIG. 11.

In FIG. 15 a connector system 48 according to a fourth embodiment is illustrated. The connector system 15 includes the connector X4 of FIG. 8, and the connector Y4 of FIG. 13. A requirement for the design of the connector system 47 of FIG. 14 is that the axial depth length M2_dl and the axial depth length F1_dl are equal within a margin. In this embodiment, M2_dl and F1_dl are equal to twice the thread length L_ths (FIG. 2). A further requirement for the design of the connector system 47 is that the axial top length M1_tl and axial top length F1_tl are equal within a margin. In this embodiment, the axial top length M1_tl and the axial top length F1_tl are equal to the thread length L_ths within a margin. Further, the axial depth length M2_dl and the axial depth length F1_dl are equal to twice the predefined axial length L_ths of the thread 15 within a margin, respectively.

In FIG. 16 a connector system 49 according to a fifth embodiment is illustrated. The connector system 49 includes a connector X5 of FIG. 8, and the connector Y1 of FIG. 9. The connector X5 has the same design as the connector X1 of FIG. 4, and thus the same base dimensions, except that the outer collar M2 has an inner diameter M2_id that is greater than a predefined dimension of the inner diameter M2_id, and that the outer diameter M2_od is greater than a predefined dimension of the outer diameter M2_od. In particular, the inner diameter M2_id is greater than the base diameter K2 with a distance ΔK22. Further, the outer diameter M2_od is greater than the base diameter K3 with a distance ΔK33.

In FIG. 17 a connector system 50 according to a sixth embodiment is illustrated. The connector system 50 includes the connector X5 of FIG. 16, and the connector Y2 of FIG. 10. The inner diameter F1_id is greater than a predefined dimension of the inner diameter F1_id, and the outer diameter F1_od is greater than a predefined dimension of the outer diameter F1_od. More particularly, the diameter F1_id of the connector Y2 is greater than the base diameter D1 with a distance ΔD11. Further, the inner diameter F1_od is greater than the base diameter D2 with a distance ΔD22.

According to some embodiments, the outer diameter M1_od of a connector X is extended to the respective outer diameter M1_ods+ΔK1, or M1_ods+ΔK1+ΔK11 by means of at least one protrusion. The at least one protrusion has a radial extension from the outer side of the inner collar M1. The number of protrusions may be any number, e.g. one, two, three, four, five, six, seven, eight etc. The inner diameter M1_od of the inner collar may thus not be uniform, and the inner collar thickness is thus not uniform. However, when referred to the inner diameter M1_od herein, it is meant the greatest inner diameter M1_od of the inner collar M1. By having protrusions instead of having a uniform thickness, the amount of material can be reduced and thus save on costs.

The disclosure also relates to a system according to the second aspect including a plurality of connector systems as described herein. An example of such a system will in the following be explained with reference to FIG. 26. However, first the general requirements for such a system will be explained.

Thus, the system includes a plurality of connector systems of which an interconnectable male single channel fluid connector X and female single channel fluid connector Y of each connector system are designed to be non-interconnectable with any of the male single channel fluid connector X and female single channel connector Y of the other connector systems of the plurality of connector systems. Also, the luer type or predefined female single channel connector YS, the luer type or predefined male single channel connector XS and any luer type or certain predefined dimension, size, length and/or diameter are the same for all the plurality of connector systems of the system.

According to a third aspect, the system includes a plurality of connector systems wherein each connector system includes a connector X being a modified male luer lock fluid connector X and a thereto interconnectable connector Y being a modified female luer lock fluid connector Y. The interconnectable modified male luer lock fluid connector X and modified female luer lock fluid connector Y of each connector system are designed to be non-interconnectable with any of the modified male luer lock fluid connectors X and the modified female luer lock fluid connectors Y of the other connector systems of the plurality of connector systems. The modified male luer lock fluid connectors X are further interconnectable with a same predefined connector YS being a standard female luer lock fluid connector YS, and the modified female luer lock fluid connectors Y are interconnectable with a same predefined connector XS being a standard male luer lock fluid connector XS. The system according to the third aspect is actually a variant of the system according to the second aspect, but specifically based on standard luer lock connectors. A connector X may thus be a modified male luer lock fluid connector X, and thus modified from a luer type or predefined male single channel connector XS being a standard male luer lock fluid connector. A connector Y may be a modified female luer lock fluid connector Y, and thus modified from a luer type or predefined female single channel connector YS being a standard female luer lock fluid connector.

In the FIGS. 18-25 a plurality of the above described connectors X and connectors Y that are designed to not be interconnected are illustrated. They are illustrated to show the beneficial selectivity of the above described connector systems, and that the connectors X, Y that indeed are not intended to be connected with each other, really are non-interconnectable. Each connector X is however designed to be connected to a corresponding mating connector Y and forms a connector system as has been previously described.

In some embodiments of the system, the plurality of connector systems includes a connector system 48 (FIG. 15)

where the axial top length F1_tl of the female single channel fluid connector Y4 is greater or equal to the axial depth length M2_dl of any male single channel fluid connector X of the other connector systems 47, 49, 50 of the plurality of connector systems 47, 48, 49, 50 described herein. The luer type or predefined female single channel connector YS and the female single channel connector Y4 have the same predefined axial length L_ths of the thread 15 on the outer side 14 of the tube 13, respectively. Further, the axial top length F1_tl is equal to the predefined axial thread length L_ths within a margin. An example is illustrated in FIG. 18, where the connector X1 of FIG. 4 and FIG. 15, and the connector Y4 of FIG. 13 are illustrated. The collar F1 of the connector Y4 is inserted into the space 22 of the connector X1. However, as the collar F1 has a top length F1_tl that equals the basic thread length L_ths, and the depth length M1_dl is equal to the basic thread length L_ths, the outer thread 15 of the connector Y4 will never be able to engage with the inner thread 9. Thus, engagement between the connector X1 and the connector Y4 is not possible.

In some embodiments of the system, the plurality of connector systems includes a connector system 15 where the top length M1_tl of the male single channel fluid connector X4 is greater or equal to the depth length F1_dl of any female single channel fluid connector Y of the other connector systems of the plurality of connector systems. Further, the luer type or predefined female single channel connector YS and the female single channel connector Y4 have a same predefined axial length L_ths of the thread 15 on the outer side 14 of the tube 13, respectively. Also, the axial depth length F1_dl is equal to the predefined axial length L_ths of the thread 15 within a margin. An example is illustrated in FIG. 19, where the connector X4 of FIG. 8 and the connector Y1 of FIG. 9 are illustrated. The inner collar M1 of the connector X4 is inserted into the space 26 of the connector Y1. However, as the inner collar M1 has a top length M1_tl that equals the basic thread length L_ths, and the depth length F1_dl is equal to the basic thread length L_ths, the inner thread 9 of the connector X4 will never be able to engage with the outer thread 15. Thus, engagement between the connector X4 and the connector Y1 is not possible.

In FIG. 20, the connector X1 of FIG. 4 and the connector Y2 of FIG. 10 are illustrated. As the outer diameter F1_id of the connector Y2 is greater than the inner diameter M2_id of the connector X1, but smaller than M2_od of the connector X1, the inner thread 9 of the connector X1 will never be able to engage with the outer thread 15 of the connector Y2. Thus, engagement between the connector X1 and the connector Y2 is not possible.

In some embodiments, the plurality of connector systems includes a connector system where the outer diameter F1_od of the female single channel fluid connector Y is greater than the inner diameter M2_id of any male single channel fluid connector of the other connector systems of the plurality of connector systems. Further, the inner diameter F1_id of the female single channel fluid connector Y is less than the outer diameter M2_od of any male single channel fluid connector X of the other connector systems of the plurality of connector systems. Examples of such connectors Y are illustrated in FIGS. 21 and 25, together with a non-interconnectable male connector X. In FIG. 21, the connector X1 of FIG. 4 and the connector Y3 of FIG. 11 are illustrated. As the outer diameter F1_id of the connector Y2 is greater than the inner diameter M2_id of the connector X1, but smaller than M2_od of the connector X1, the collar F1 will not be able to be received into the space 22. Thus, the inner thread 9 of the connector X1 will never be able to engage with the outer thread 15 of the connector Y2, and engagement between the connector X1 and the connector Y2 is not possible. In FIG. 25, the connector X2 of FIG. 5 and the connector Y3 of FIG. 11 are illustrated. As the inner diameter F1_id of the connector Y3 is greater than the inner diameter M2_id of the connector X2, but smaller than M2_od of the connector X2, the inner thread 9 of the connector X2 will never be able to engage with the outer thread 15 of the connector Y3. Thus, engagement between the connector X2 and the connector Y3 is not possible.

Figure 23:
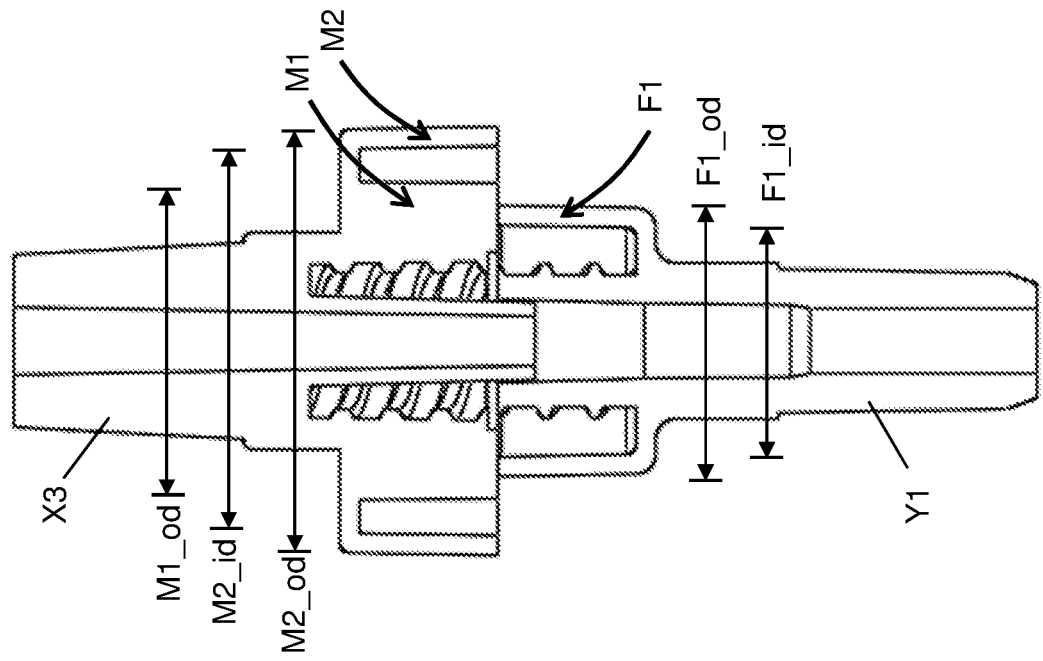
Figure 22:
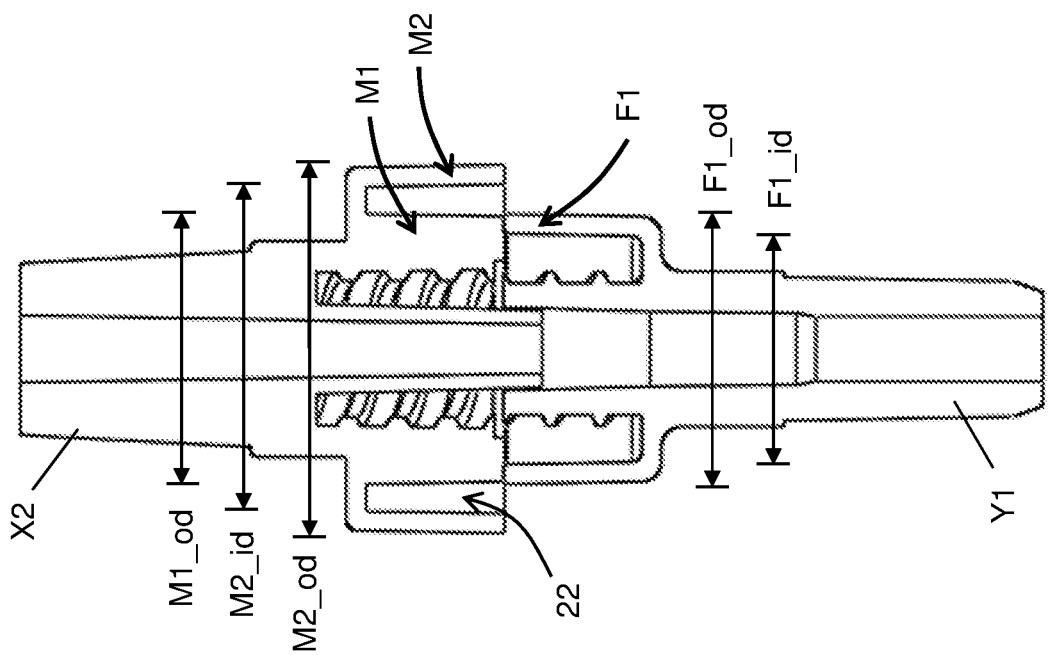

In some embodiments of the system, the plurality of connector systems includes a connector system 47, 49, 50 where the inner diameter F1_id of the female single channel fluid connector Y is less than the outer diameter M1_od of any male single channel fluid connector X of the other connector systems of the plurality of connector systems. Examples of such connectors Y are illustrated in FIGS. 22, 23 and 24, together with a non-interconnectable male connector X. In FIG. 22, the connector X2 of FIG. 5 and the connector Y1 of FIG. 9 are illustrated. As the inner diameter M1_od of the connector X2 is greater than the inner diameter F1_id, the collar F1 will not be able to be received into the space 22. Thus, the inner thread 9 of the connector X2 will never be able to engage with the outer thread 15 of the connector Y1, and engagement between the connector X2 and the connector Y1 is not possible. In FIG. 23, the connector X3 of FIG. 6 and the connector Y1 of FIG. 9 are illustrated. As the inner diameter M1_od of the connector X3 is greater than the inner diameter F1_id of the connector Y1, the collar F1 will not be able to be received into the space 22. Thus, the inner thread 9 of the connector X2 will never be able to engage with the outer thread 15 of the connector Y1, and engagement between the connector X3 and the connector Y1 is not possible. In FIG. 24, the connector X3 of FIG. 6 and the connector Y2 of FIG. 10 are illustrated. As the inner diameter M1_od of the connector X3 is greater than the inner diameter F1_id of the connector Y2, the collar F1 will not be able to be received into the space 22. Thus, the inner thread 9 of the connector X3 will never be able to engage with the outer thread 15 of the connector Y2, and engagement between the connector X3 and the connector Y2 is not possible.

Figure 26:
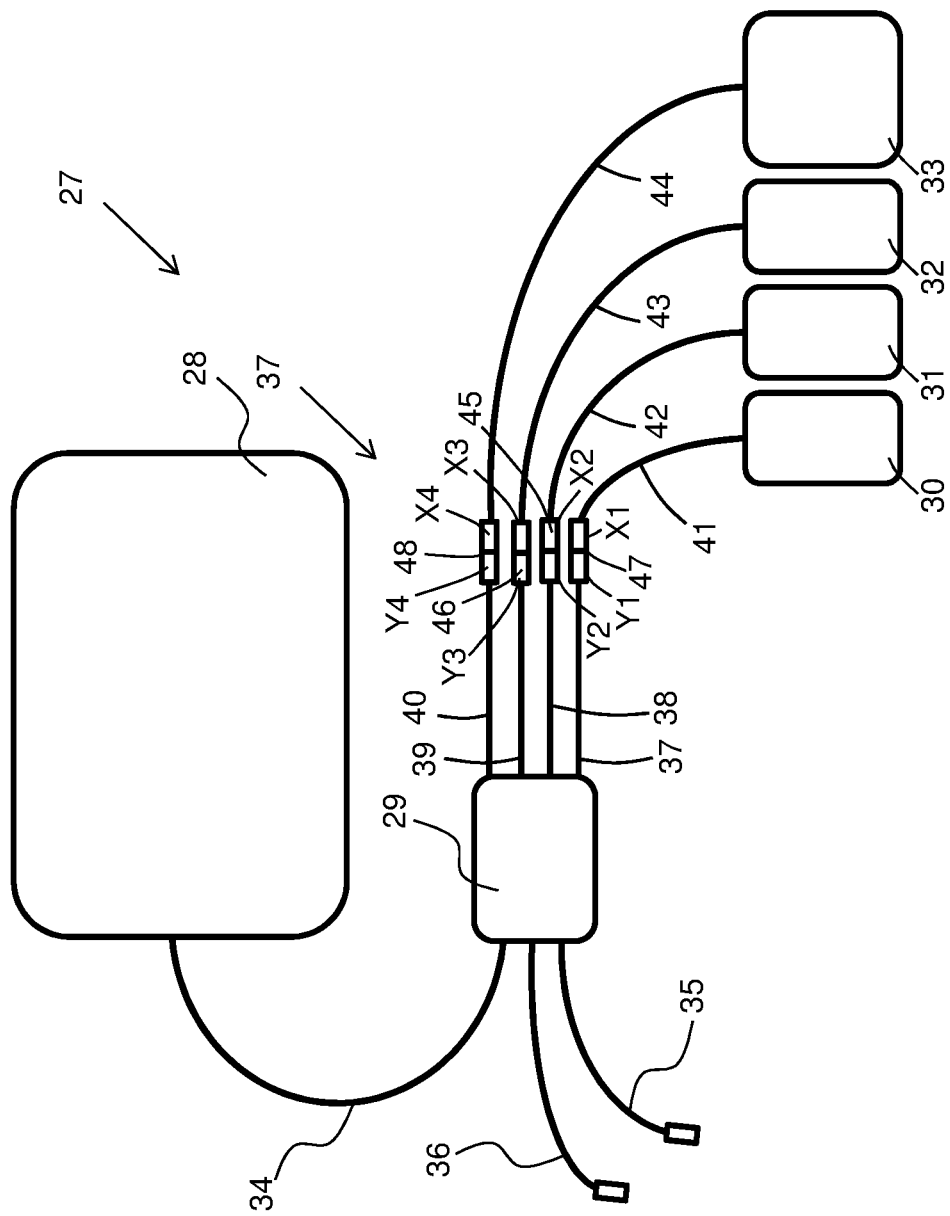
FIG. 26 is illustrating a fluid line set including a system with four connector systems for connecting fluid bags in a peritoneal dialysis (PD) system.

The system with a plurality of connector systems can be used in a plurality of different applications. One application is for peritoneal dialysis (PD). PD is in general performed using ready to use bags with fluid containing different amounts of glucose, usually 1.5%, 2.5%, or 4% glucose. The fluid is infused into the peritoneal cavity via a peritoneal catheter 3-5 times every 24 hours, after drainage of the fluid from the previous fill. In some cases the exchange of fluid can be performed using a cycle machine taking care of the filling and drainage automatically, typically during the night when the patient is sleeping. This type of PD is called Automated Peritoneal Dialysis (APD). The APD treatment is usually performed using ready to use PD fluid contained in a number of bags for every night of treatment, usually 10-20 L in total. A line set is used for supplying the PD solution to the patient via the peritoneal catheter. The fluid volume infused to the peritoneal cavity of the patient is exchanged a number of times during the night. The glucose strength of the fluid used varies and a number of different glucose strengths may be used during the same treatment. In FIG. 26 an example of a line set 27 is illustrated. The line set 27 includes a cassette 29 whereto the PD-solutions are passed for dosing. When in use, the cassette 29 is inserted into the cycler machine and the cycler machine is arranged to actuate membrane pumps and vents in the cassette 29 in order to dose and pass fluids to a heating bag 28. The heating bag 28 is intended to be put on a heater of the cycler machine in order to warm the PD-fluid e.g. to body temperature before use. Bags with fluids are connected to the cassette 29, and it is important that the bags with different fluids are connected to a right connector. For example may two, three or more fluids be needed to produce a final ready to use a final ready to use PD fluid, for example buffer concentrate and glucose concentrate. If e.g. a bag containing a buffer concentrate has been connected to the connector supposed to be used for the glucose concentrate the final PD fluid may become dangerous to use. Therefore, the line set 27 of FIG. 26 is provided with a system 37 of the invention, including a plurality of the connector systems 47, 15, 45, 46 as have been previously described. The system is connecting the plurality of fluid bags 30, 31, 32, 33 to the line set 27. Further, heater line 34 is arranged for connecting the cassette 29 to the heating bag 28, and a patient line 35 is arranged for connecting the cassette 29 to the catheter arranged in the peritoneal cavity of a patient (not shown), and thus introduction of PD fluid from the heating bag 28 to the peritoneal cavity of the patient. A drain line 36 is arranged for connecting the cassette 29 to a drain (not shown). A plurality of solution lines 37, 38, 39, 40 is arranged for connecting at one end to the cassette 29 and at the other end to a respective connector X of a connector system 47, 15, 45, 46. A plurality of bag lines 41, 42, 43, 44 is arranged for connecting at one end to a respective of the plurality of fluid bags 30, 31, 32, 33, and at the other end to a respective other connector Y of the connector system 47, 15, 45, 46. Thus, a first fluid line 37 is at one end arranged to the cassette 29 and at the other end to the connector X1 of the first connector system 47, and a first bag line 41 is connected at one end to the connector Y1 of the first connector system 47 and at the other end to a first fluid bag 30. A second fluid line 38 is at one end arranged to the cassette 29 and at the other end to the connector X2 of the second connector system 45, and a second bag line 42 is connected at one end to the connector Y2 of the second connector system 45 and at the other end to a second fluid bag 31. A third fluid line 39 is at one end arranged to the cassette 29 and at the other end to the connector X3 of the third connector system 46, and a third bag line 43 is connected at one end to the connector Y3 of the third connector system 46 and at the other end to a third fluid bag 32. A fourth fluid line 40 is at one end arranged to the cassette 29 and at the other end to the connector X4 of the fourth connector system 15, and a fourth bag line 44 is connected at one end to the connector Y4 of the fourth connector system 15 and at the other end to a fourth fluid bag 33.

During the setup of the PD system, the connectors Y1, Y2, Y3, Y4 are connected by an operator, e.g. the patient, with a respective corresponding interconnectable connector X1, X2, X3, X4. As the two connectors X, Y of the respective connector system 47, 15, 45, 46 are interconnectable, but non-interconnectable with any other connector of the other connector systems 47, 15, 45, 46 there is no risk for misconnection of any connectors of the system 37. The system 37 makes it impossible to connect the different concentrates to more than one of the plurality of connectors Y of the fluid cassette 29. At the same time there may be situations when it is necessary to use standard fluids e.g. two to three conventional APD fluid bags containing 5-6 L of ready to use fluid to perform the treatment. The conventional fluid bags have standard connectors, and are thus interconnectable with the connectors of the system.

Various other applications for the system are possible. For example, there are a number of infusion fluids that can be administered via catheters in different types of blood vessels, while other needs to be administered only in one kind of vessel. To make it possible to administer e.g. saline in all kinds of catheters, a standard luer is placed on this type of bag. Another fluid, like highly osmotic parenteral nutrition fluids is only suitable to be administered to a first kind of blood vessel and the fluid bag with the another fluid would then need a first modified connector according to any of the embodiments illustrated in any of the FIGS. 4 to 13. A still another fluid should only be given in a second type of blood vessel and should then be provide with a second modified connector according to any of the embodiments illustrated in any of the FIGS. 4 to 13, but different from the first modified connector. This will make it possible to avoid giving fluids in the wrong blood vessel but still be able to give standard infusions in all kinds of vessels without the use of adaptors or separate catheters.

Further, there are a number of different fluids used intravenously that are incompatible due to the risk for precipitation and formation of particles, e.g. bicarbonate containing fluids and calcium containing fluid. If one or several connector systems according to the embodiments herein it is possible to selectively make it impossible to connect fluid bags of incompatible fluids to the same connector but still make it possible to connect the bags fitted with the special connector to a standard luer if that is needed.

Another use for the system is when using cytostatic drugs. Cytostatic drugs are generally not allowed to be infused in a peripheral vein and shall instead be infused via a central vein. Any infusion lines to a peripheral vein may then be provided with a modified connector according to any of the embodiments illustrated in FIGS. 4 to 13, and a bag with cytostatic drug to be infused is provided with another modified connector of another connector system of the same system. Thereby it will become impossible to connect a bag with cytostatic drug to any peripheral vein. There may however still be a need to connect e.g. a saline bag with a standard luer connector to a modified connector of the infusion line to a peripheral vein after administration of the highly toxic substance, which will be possible as any modified connector also is connectable to a corresponding non-modified standard luer connector.

A still another use for the system is in hemodialys (HD), when using a plurality of solutions that shouldn't be mixed up. For example, the system may be used in potassium profiled dialysate (AFBK) to provide selectivity, where up to three different bags with solution to be administered should not be mixed up.

FIG. 27 is illustrating a connectivity scheme for a system according to the second aspect and/or the third aspect. The rows includes the male connectors X according to the first to sixth embodiment of connectors X, plus the luer type or predefined connector XS that is interconnectable with all the female connectors Y. The rows include female connectors Y according to the first to sixth embodiment of connectors Y, plus the luer type or predefined connector YS that is interconnectable with all the male connectors X. A plus "+" indicates that the corresponding male connector X and the female connector Y are interconnectable to form a fluid tight coupling. A zero "0" indicates that the corresponding male connector X and the female connector Y are non-interconnectable to form a fluid tight coupling. Thus, the connector XS and the connector YS form the connector system as illustrated in FIG. 3. The connector X1 and the connector Y1 form the connector system 47 (FIG. 14) according to the first embodiment of the connector systems. The connector X2 (FIG. 5) and the connector Y2 (FIG. 10) form the connector system 45 according to the second embodiment of the connector systems. The connector X3 (FIG. 6) and the connector Y3 (FIG. 11) form the connector system 46 according to the third embodiment of the connector systems. The connector X1_X4, or simply X4, and the connector Y1_Y4, or simply Y4, form the connector system 48 according to the fourth embodiment of the connector systems (FIG. 15). The connector X2_X4 (FIGS. 5, 8), and the connector Y2_Y4 (FIGS. 10, 13), form a connector system according to a seventh embodiment of the connector systems. The connector X3_X4 (FIGS. 6, 8), and the connector Y3_Y4 (FIGS. 11, 13), form a connector system according to an eighth embodiment of the connector systems. The plurality of connector systems of the system may thus include a plurality or all of the connector systems according to the first, the second, the third, the fourth, the seventh and the eighth embodiments of the connector systems. Each of these connector systems includes an interconnectable male connector X and female connector Y, that are non-interconnectable with any of the connectors X, Y of the other connector systems of the plurality of connector systems.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A connector system for a medical application, the connector system comprising:
 a male single channel fluid connector designed with an inner tube for passing fluid, and a center collar with a threaded inner side and arranged concentric with the inner tube, the center collar being defined by an outer diameter and an inner diameter;
 a female single channel fluid connector designed with a tube for passing fluid, the tube having a threaded outer side,
 wherein the male single channel fluid connector is designed with an outer collar arranged concentric with the inner tube outside the center collar of the male single channel fluid connector, the outer collar of the male single channel fluid connector is defined by an inner diameter and an outer diameter and a space in between the center collar and the outer collar defining a depth stop,
 wherein the space of the male single channel fluid connector has an axial depth length,
 wherein the female single channel fluid connector further is designed with an outer collar arranged concentric with the tube and defined by an inner diameter and an outer diameter, and a space in between the tube and the outer collar defining a depth stop of the female single channel fluid connector,
 wherein the space of the female single channel fluid connector has an axial depth length,
 wherein the outer diameter of the center collar of the male single channel fluid connector, the inner diameter of the outer collar of the male single channel fluid connector, the inner diameter of the center collar of the male single channel fluid connector, the outer diameter of the outer collar of the female single channel fluid connector, the depth length of the outer collar of the male single channel fluid connector, and the depth length of the outer collar of the female single channel fluid connector are designed such that the male single channel fluid connector is interconnectable both with:
 the female single channel fluid connector with the outer collar such that the outer collar of the female single channel fluid connector is received inside the space of the male single channel fluid connector, and
 a luer type female single channel fluid connector with a tube for passing of fluid having a threaded outer side with the same design and dimension as the tube and threaded outer side as of the female single channel fluid connector to form a fluid tight single channel connection for passage of fluid, and
 wherein the female single channel fluid connector also is interconnectable with:
 a luer type male single channel fluid connector with an inner tube for passing of fluid, and a center collar with a threaded inner side with the same design and dimension as the inner tube and the threaded inner side as of the male single channel fluid connector to form a fluid tight single channel connection for passage of fluid.

2. The connector system according to claim 1, wherein the inner diameter of the outer collar of the female single channel fluid connector is greater than the outer diameter of the center collar of the male single channel fluid connector, and
 wherein the outer diameter of the outer collar of the female single channel fluid connector is smaller than the inner diameter of the outer collar of the male single channel fluid connector.

3. The connector system according to claim 2, wherein the outer diameter of the center collar of the male single channel fluid connector is greater than a predefined standard outer diameter of the luer type male single channel fluid connector, and/or
 wherein the inner diameter of the outer collar of the male single channel fluid connector is greater than a first base inner diameter of the luer type male single channel fluid connector, and/or
 wherein the inner diameter of the outer collar of the female single channel fluid connector is greater than a second base inner diameter of the luer type female single channel fluid connector, and/or
 wherein the outer diameter of the outer collar of the female single channel fluid connector is greater than a third base outer diameter of the luer type female single channel fluid connector, wherein the first base inner diameter is greater than the third base outer diameter, and the second base inner diameter is smaller than the third base outer diameter.

4. The connector system according to claim 2, wherein the inner diameter of the center collar of the male single channel fluid connector is non-uniform.

5. A system including a plurality of connector systems according to claim 1, wherein the interconnectable male single channel fluid connector and female single channel fluid connector of each connector system are designed to be non-interconnectable with any of the male single channel fluid connector and female single channel fluid connector of the other connector systems of the plurality of connector systems.

6. The system according to claim 5, wherein the plurality of connector systems includes a connector system where an axial top length of the outer collar of the female single channel fluid connector is greater or equal to the axial depth length of the outer collar of any male single channel fluid connector of the other connector systems of the plurality of connector systems, wherein the luer type female single channel fluid connector and the female single channel fluid connector have a same predefined axial length of a thread on the outer side of the tube, respectively, and wherein the axial top length of the outer collar of the female single channel fluid connector is equal to the predefined axial length of the thread within a fifth margin.

7. The system according to claim 5, wherein the plurality of connector systems includes a connector system where the top length of the center collar of the male single channel fluid connector is greater or equal to the depth length of the outer collar of any female single channel fluid connector of the other connector systems of the plurality of connector systems, and
   wherein the luer type female single channel fluid connector and the female single channel fluid connector have a same predefined axial length of a thread on the outer side of the tube, respectively, and wherein the axial depth length of the outer collar of the female single channel fluid connector is equal to the predefined axial length of the thread within a sixth margin.

8. The system according to any of the claims 5, wherein the plurality of connector systems includes a connector system where the inner diameter of the outer collar of the female single channel fluid connector is less than the outer diameter of the center collar of any male single channel fluid connector of the other connector systems of the plurality of connector systems, or
   wherein the outer diameter of the outer collar of the female single channel fluid connector is greater than the inner diameter of the outer collar of any male single channel fluid connector of the other connector systems of the plurality of connector systems, and
   wherein the inner diameter of the outer collar of the female single channel fluid connector is less than the outer diameter of the outer collar of any male single channel fluid connector of the other connector systems of the plurality of connector systems.

9. The connector system of claim 1, wherein the center collar of the male single channel fluid connector is designed to have an axial top length extending beyond the outer collar of the male single channel fluid connector, and wherein the outer collar of the female single channel fluid connector is designed to have an axial top length extending beyond the tube.

10. The connector system according to claim 9, wherein the axial depth length of the outer collar of the male single channel fluid connector and the axial depth length of the outer collar of the female single channel fluid connector are equal within a first margin, and wherein the axial top length of the center collar of the male single channel fluid connector and the axial top length of the outer collar of the female single channel fluid connector are equal within a second margin.

11. The connector system according to claim 10, wherein the luer type female single channel fluid connector and the female single channel fluid connector have a same predefined axial length of a thread on the outer side of the tube, respectively, and wherein the axial top length of the center collar of the male single channel fluid connector and the axial top length of the outer collar of the female single channel fluid connector are equal to the predefined axial length of the thread within a third margin, respectively, and wherein the axial depth length of the outer collar of the male single channel fluid connector and the axial depth length of the outer collar of the female single channel fluid connector are equal to twice the predefined axial length of the thread within a fourth margin, respectively.

12. A system including a plurality of connector systems, wherein each connector system includes a modified male luer lock fluid connector and a thereto interconnectable modified female luer lock fluid connector, wherein the interconnectable modified male luer lock fluid connector and modified female luer lock fluid connector of each connector system are designed to be non-interconnectable with any of the modified male luer lock fluid connectors and modified female luer lock fluid connectors of the other connector systems of the plurality of connector systems, and wherein the modified male luer lock fluid connectors are interconnectable with a same standard female luer lock fluid connector, and the modified female luer lock fluid connectors are interconnectable with a same standard male luer lock fluid connector.

13. A connector system for a medical application, the connector system comprising:
   a male fluid connector including an inner tube for passing fluid and a center collar having a threaded inner side, the center collar arranged concentric with the inner tube and defined by an outer diameter;
   a female fluid connector including a tube for passing fluid, the tube having a threaded outer side;
   wherein the male fluid connector includes an outer collar arranged concentric with the inner tube outside the center collar of the male fluid connector, the outer collar of the male fluid connector defined by an inner diameter and an outer diameter and a space in between the center collar and the outer collar defining a depth stop, wherein the space of the male fluid connector has an axial depth;
   wherein the center collar of the male fluid connector includes an axial top length extending beyond the outer collar of the male fluid connector;
   wherein the female fluid connector further includes an outer collar arranged concentric with the tube, the outer collar defined by an inner diameter and an outer diameter, and a space in between the tube and the outer collar defining a depth stop of the female fluid connector, wherein the space of the female fluid connector includes an axial depth;
   wherein the outer collar of the female fluid connector includes an axial top length extending beyond the tube;
   wherein the outer diameter of the center collar of the male fluid connector, the inner diameter of the outer collar of the male fluid connector, the inner diameter of the center collar of the male fluid connector, the outer diameter of the outer collar of the female single channel fluid connector, the depth length of the outer collar of the male fluid connector, the depth length of the outer collar of the female fluid connector, the top length of the center collar of the male fluid connector, and the top length of the outer collar of the female fluid connector are configured such that the male fluid connector is interconnectable with both:
      the female fluid connector with the outer collar such that the outer collar of the female fluid connector is received inside the space of the male fluid connector, and
      a luer type female fluid connector including a tube for passing fluid having a threaded outer side to form a fluid tight connection for passage of fluid, and
   wherein the female fluid connector is also interconnectable with:

a luer type male fluid connector including an inner tube for passing fluid, and a center collar including a threaded inner side to form a fluid tight connection for passage of fluid.

\* \* \* \* \*